(12) United States Patent
Hilfinger et al.

(10) Patent No.: US 9,181,281 B2
(45) Date of Patent: Nov. 10, 2015

(54) PRODRUGS OF NEURAMINIDASE INHIBITORS

(71) Applicants: John Hilfinger, Ann Arbor, MI (US); Gordon Amidon, Ann Arbor, MI (US)

(72) Inventors: John Hilfinger, Ann Arbor, MI (US); Gordon Amidon, Ann Arbor, MI (US)

(73) Assignee: SineVir Therapeutics LLC, Ann Arbor, MI (US)

( * ) Notice: Subject to any disclaimer, the term of this patent is extended or adjusted under 35 U.S.C. 154(b) by 0 days.

(21) Appl. No.: 14/091,004

(22) Filed: Nov. 26, 2013

(65) Prior Publication Data

US 2014/0155350 A1    Jun. 5, 2014

Related U.S. Application Data

(63) Continuation of application No. 12/937,624, filed as application No. PCT/US2009/040660 on Apr. 15, 2009, now abandoned.

(60) Provisional application No. 61/045,104, filed on Apr. 15, 2008.

(51) Int. Cl.

| *C07C 279/16* | (2006.01) |
|---|---|
| *C07F 7/12* | (2006.01) |
| *A61K 31/155* | (2006.01) |
| *A61K 31/167* | (2006.01) |
| *A61K 31/351* | (2006.01) |
| *C07D 231/14* | (2006.01) |
| *C07D 307/89* | (2006.01) |
| *C07D 309/28* | (2006.01) |

(52) U.S. Cl.
CPC .......... *C07F 7/12* (2013.01); *A61K 31/155* (2013.01); *A61K 31/167* (2013.01); *A61K 31/351* (2013.01); *C07C 279/16* (2013.01); *C07D 231/14* (2013.01); *C07D 307/89* (2013.01); *C07D 309/28* (2013.01)

(58) Field of Classification Search
None
See application file for complete search history.

(56) References Cited

U.S. PATENT DOCUMENTS

| 4,732,890 A * | 3/1988 | Bonelli et al. ............... 514/15.7 |
|---|---|---|
| 5,360,817 A | 11/1994 | von Izstein et al. |
| 5,648,379 A | 7/1997 | Von Itzstein et al. |
| 5,763,483 A | 6/1998 | Bischofberger et al. |
| 5,866,601 A | 2/1999 | Lew et al. |
| 5,952,375 A | 9/1999 | Bischofberger et al. |
| 6,225,341 B1 | 5/2001 | Bischofberger et al. |
| 6,451,766 B1 | 9/2002 | Honda et al. |
| 2003/0171303 A1 | 9/2003 | Gallop et al. |
| 2005/0070715 A1 * | 3/2005 | Bhat et al. .................... 546/315 |
| 2005/0137141 A1 | 6/2005 | Hilfinger |
| 2007/0099917 A1 | 5/2007 | Nice et al. |
| 2007/0135525 A1 | 6/2007 | Liang et al. |
| 2007/0167353 A1 | 7/2007 | Hilfinger et al. |
| 2007/0275900 A1 | 11/2007 | Balzarini |

FOREIGN PATENT DOCUMENTS

| EP | 1336602 A1 | 8/2003 |
|---|---|---|
| WO | 01/20331 A1 | 6/2001 |
| WO | 2006/027711 A1 | 3/2006 |
| WO | 2007/087056 A2 | 8/2007 |

OTHER PUBLICATIONS

Waghorn et al ('Zanamivir Drugs' May 1998 v55(5) pp. 721-725).*
Board decision in U.S. Appl. No. 10/972,729 dated Feb. 15, 2012, 9 total pages.*
Board decision in U.S. Appl. No. 11/690,528 dated Jun. 14, 2012, 8 total pages.*
Guzzo P., et al., "Preparation of optically active (acyloxy)alkyl esters from optically active 0-acyl-alph-hydroxy acids", Tetrahedron Letters, vol. 43, 2002, pp. 5685-5689.
Han H., et al., "Cellular uptake mechanism of amino acid ester prodrugs in Caco-2/hPEPT1 cells overexpressing a human peptide transporter", Pharmaceutical Research, vol. 15, 1998, pp. 1382-1386.
International Search Report PCT/US2009/040660, Dated Dec. 1, 2009.
Liu Z., et al., "Synthesis and Anti-Influenza Activities of Carboxyl Alkoxyalkyl Esters of 4-guanidino-Neu5Ac2en (zanamivir)", Biorganic and Medicinal Chemistry Letters 2007, pp. 4851-4854, vol. 17.
Stella V. J., "Prodrugs:some thoughts and current issues", Journal of Pharmaceutical Sciences, vol. 99, No. 12, 2010 pp. 4755-4765.
Sun J., "Intestinal absorption of low permeability drugs: a transporter- and enzyme-targeted approach", University of Michigan Thesis, 2010, pp. i-xii and pp. 1-95.
Testa B., "Prodrug Research:Futile or Fertile", Biorganic Pharmacology 2004, pp. 2097-2106, vol. 68.
Yamashita M., et al., "CS-8958, a Prodrug of the New Neuraminidase Inhibitor R-125489, Shows Long-Acting Anti-Influenza Virus Activity", Antimicrobial Agents and Chemotherapy, 2009, pp. 186-192, vol. 53, No. 1.

* cited by examiner

*Primary Examiner* — James H Alstrum Acevedo
*Assistant Examiner* — Ronald Niebauer
(74) *Attorney, Agent, or Firm* — Honigman Miller Schwartz and Cohn LLP; Cynthia M. Bott; Jonathan P. O'Brien

(57) ABSTRACT

A new class of neuramidase inhibitor prodrugs is provided characterized by a prodrug moiety of a carboxyl group modified to form a carbonyl ethoxy amino acid, a carbonyl ethoxy dipeptide or a carbonyl ethoxy tripeptide, a guanidine group modified to form a carbonyl ethoxy amino acid, a carbonyl ethoxy dipeptide, a carbonyl ethoxy tripeptide; a primary alcohol modified to form an esterified single amino acid, dipeptide or tripeptide of zanavimir of the unaltered therapeutic agent. Exemplary therapeutic agents so modified to form prodrugs include zanavimir, oseltamivir and peramivir. The prodrug has increased oral bioavailability relative to the unaltered neuraminidase inhibitor and is effective in the inhibition of viral infections involving neuraminidase in the viral reproductive cycle.

10 Claims, 5 Drawing Sheets

Zan-Val

GOC-Val

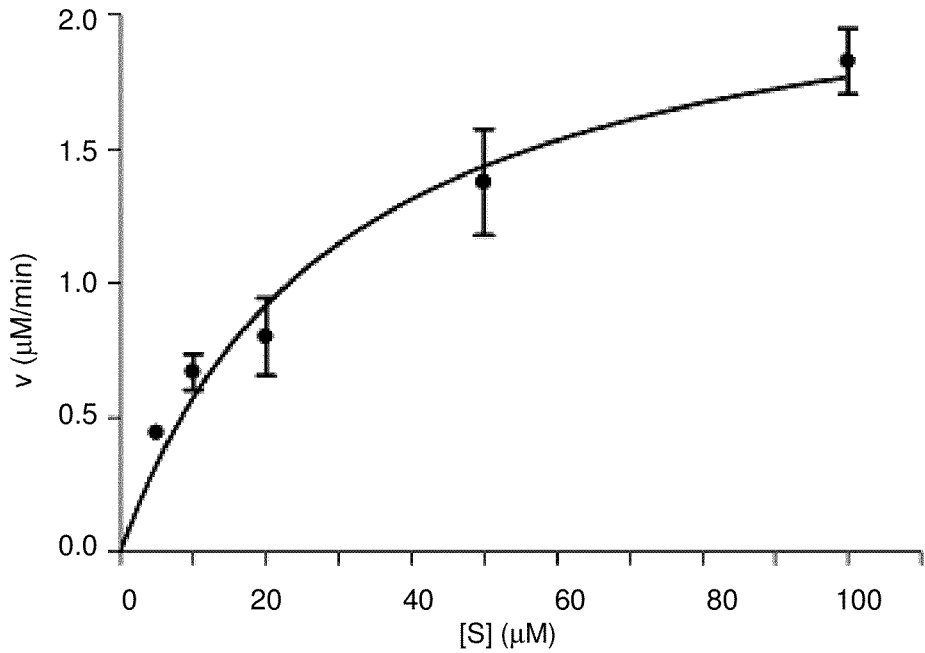
3-HPG-Val
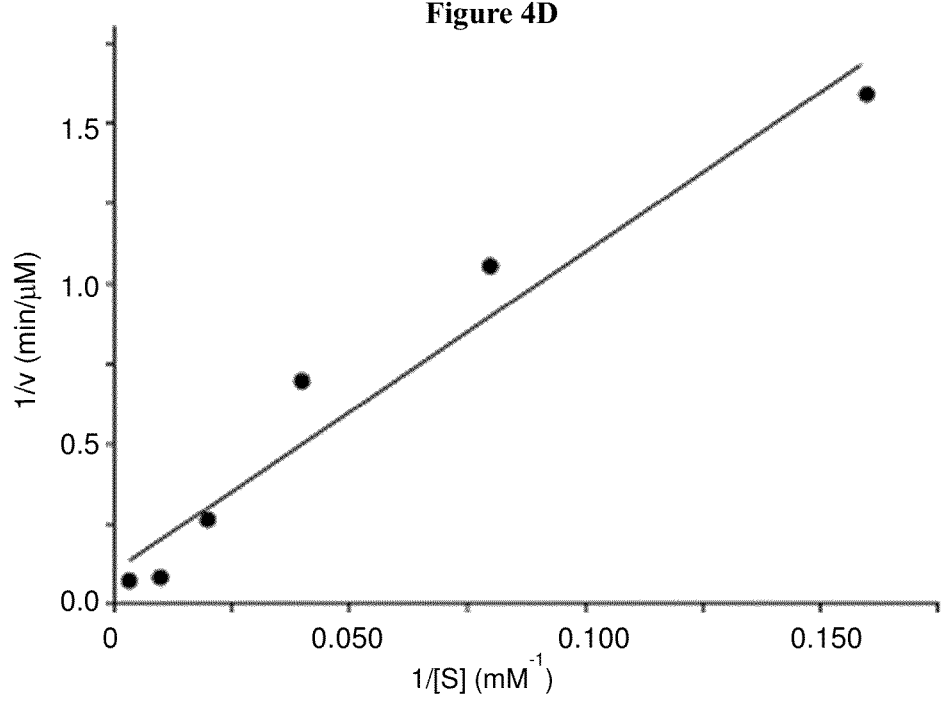
Zan-Val

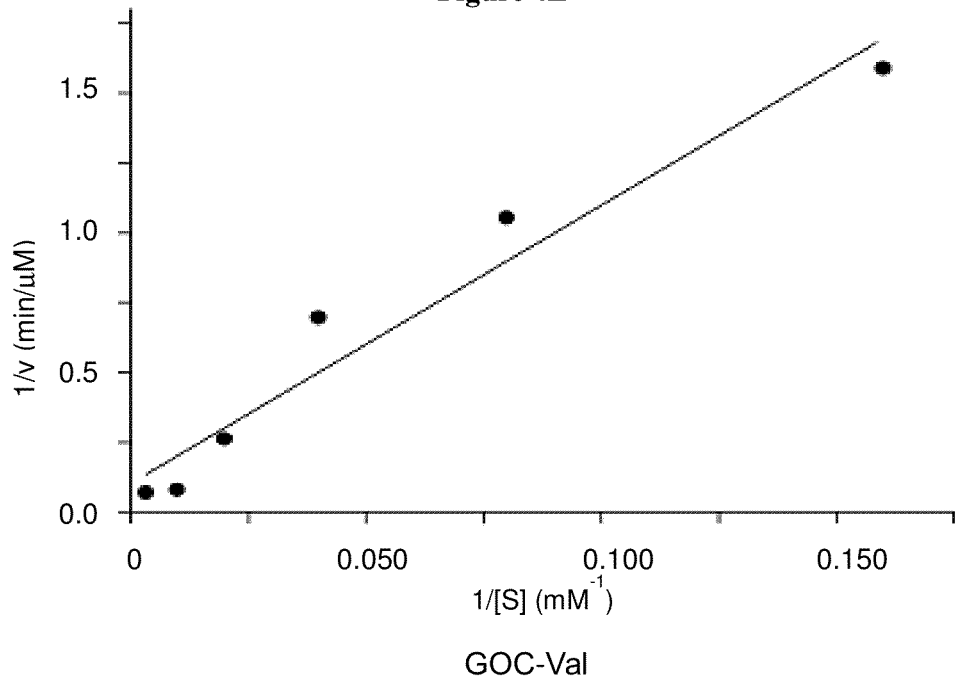
GOC-Val
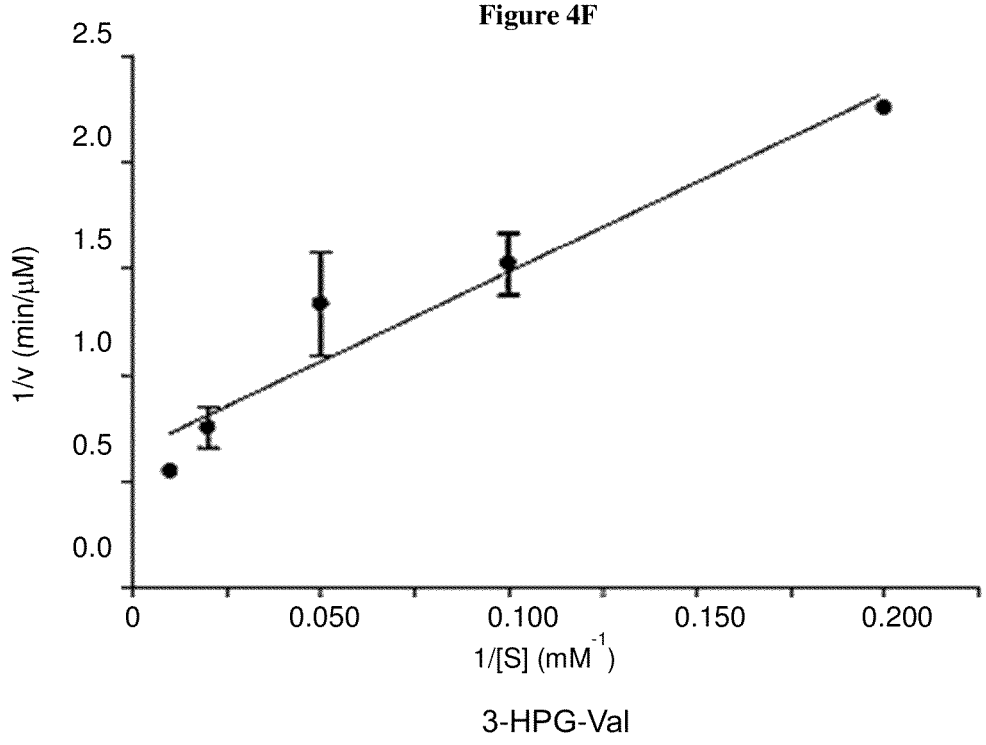
3-HPG-Val

PRODRUGS OF NEURAMINIDASE INHIBITORS

CROSS-REFERENCE TO RELATED APPLICATIONS

This application is a continuation of U.S. Ser. No. 12/937,624, filed on Nov. 22, 2010, which is a national stage application under 35 U.S.C. 371 of PCT/US2009/040660, filed Apr. 15, 2009, which claims priority of U.S. Provisional Patent Application Ser. No. 61/045,104, filed Apr. 15, 2008. The entire content of all of the above referenced applications are incorporated herein by reference.

FIELD OF THE INVENTION

The present invention in general relates to neuraminidase inhibitor prodrugs, and in particular to neuraminidase inhibitor amino acid prodrugs that provide modified bioavailability and active cellular transport relative to the drug itself.

BACKGROUND OF THE INVENTION

Numerous potentially effective therapeutic agents often exhibit poor bio-pharmaceutical properties. This problem, which can preclude the effective oral use of a potential therapeutic agent, is generally targeted with analog methodology, screening ligands, for the biopharmaceutical properties of permeability and metabolism. However, this approach can lead to less desirable drug candidates because properties that optimize biopharmaceutical properties of a molecule may not be the properties or structure that optimize its ligand binding and ultimate efficacy.

A problem associated with rendering a poorly soluble therapeutic agent orally bioavailable is that the transport and release of the active agent from a transport species are unpredictable. Amino acid and peptide transporters and identification of cells having amino acid and peptide transporter activity are known in the art. For example, PEPT1 and/or PEPT2 are known transporters as described in references [29]-[36]. Yet a robust delivery prodrug actively transported into cells bearing PEPT1 and/or PEPT2 transport receptors has remained elusive.

Thus, there exists a need for novel bioavailable drug compositions and processes for synthesis and therapeutic use of the same.

SUMMARY OF THE INVENTION

A prodrug of a neuraminidase inhibitor is provided having the formula (I):

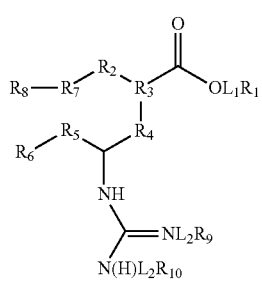

(I)

where $R_1$ is an amino acid residue having the formula —C(O)CH(R')NH$_2$, a dipeptide residue having the formula —C(O)(CH$_2$)$_n$CH(R')N(H)C(O)(CH$_2$)$_n$CH(R'')NH$_2$, a tripeptide residue having the formula —C(O)(CH$_2$)$_n$CH(R')N(H)C(O)(CH$_2$)$_n$CH(R'')N(H)C(O)(CH$_2$)$_n$CH(R''')NH$_2$, —H, —COC(CH$_3$)$_2$CH$_2$R*, —COCH$_2$CH$_2$R* or —COCH$_3$; n is zero, one or two (corresponding to an α, β or γ amino acid, respectively); $R_2$ is a nullity or —CR*R**, —O or —CR*(OH); R* is —H, —C$_1$-C$_8$ alkyl, or —C$_1$-C$_6$ alkyl having a heteroatom substituent of hydroxyl, carboxyl, or primary amine; R** is R* or an electron of covalent bond; $R_3$ is an sp$^2$ hybridized C or CR*; $R_4$ is CR*R** when $R_3$ is CR* and an sp$^2$ hybridized C when $R_3$ is the sp$^2$ hybridized C forming an ethylenic unsaturation therebetween, $R_4$ is —CH; $R_5$ is —CR*R and R is the electron of a covalent bond when bonded to $R_2$ or $R_7$ to form a 5- or 6-member cyclic structure; $R_6$ is —NH—C(O)—CH$_2$R*, $R_7$ is a nullity, —CR*R** and $R_8$ is —CR*(OR$_{11}$)CR*(OR$_{12}$)CHR*(OR$_{13}$); R$_{11}$, R$_{12}$ and R$_{13}$ are each independently an amino acid residue having the formula —C(O)(CH$_2$)$_n$CH(R')NH$_2$, a dipeptide residue having the formula —C(O)(CH$_2$)$_n$CH(R')N(H)C(O)(CH$_2$)$_n$CH(R'')NH$_2$, a tripeptide residue having the formula —C(O)(CH$_2$)$_n$CH(R')N(H)C(O)(CH$_2$)$_n$CH(R'')N(H)C(O)(CH$_2$)$_n$CH(R''')NH$_2$, —H, —COC(CH$_3$)$_2$CH$_2$R*, —COCH$_2$CH$_2$R*, or —COCH$_3$; $R_9$ and $R_{10}$ are each independently an amino acid residue having the formula —C(O)(CH$_2$)$_n$CH(R')NH$_2$, a dipeptide residue having the formula —C(O)(CH$_2$)$_n$CH(R')N(H)C(O)(CH$_2$)$_n$CH(R'')NH$_2$, a tripeptide residue having the formula —C(O)(CH$_2$)$_n$CH(R')N(H)C(O)(CH$_2$)$_n$CH(R'')N(H)C(O)CH(R''')NH$_2$ or —H; $L_1$ is a nullity, —[(CH$_2$)$_n$CH(CH$_2$R*)O]$_m$ or —[(CH$_2$)$_n$CH$_2$O]$_m$, with the proviso that $L_1$ is —[(CH$_2$)$_n$CH(CH$_2$R*)O]$_m$ or —[(CH$_2$)$_n$CH$_2$O]$_m$ when $R_1$ is a single amino acid residue, a dipeptide residue or a tripeptide residue; m is 1; $L_2$ is a nullity, —C(O)(CH$_2$)$_n$CH(CH$_2$R*)O or —C(O)O(CH$_2$)$_n$CH$_2$O with the proviso that $L_2$ is —C(O)[(CH$_2$)$_n$CH(CH$_2$R*)O]$_m$ or —C(O)O[(CH$_2$)$_n$CH$_2$O]$_m$ when $R_9$ or $R_{10}$ is a single amino acid residue or a dipeptide residue; R', R'' and R''' are in each occurrence independently selected amino acid side chain; with the proviso that at least one of $R_1$, $R_9$, $R_{10}$, $R_{11}$, $R_{13}$ or $R_{13}$ is a single α, β or γ amino acid residue, a dipeptide residue or a tripeptide residue. In a specific preferred embodiment of the prodrug of formula (I) n is zero in each occurrence and R* is H in each occurrence. The prodrug has increased oral bioavailability relative to the unaltered neuraminidase inhibitor and is effective in the inhibition of viral infections involving neuraminidase in the viral reproductive cycle.

BRIEF DESCRIPTION OF THE DRAWINGS

FIGS. 4A-4F are Michaelis-Menten and Lineweaver-Burk plots for the inventive prodrugs of FIG. 3.

DETAILED DESCRIPTION OF THE PREFERRED EMBODIMENTS

Figure 1:
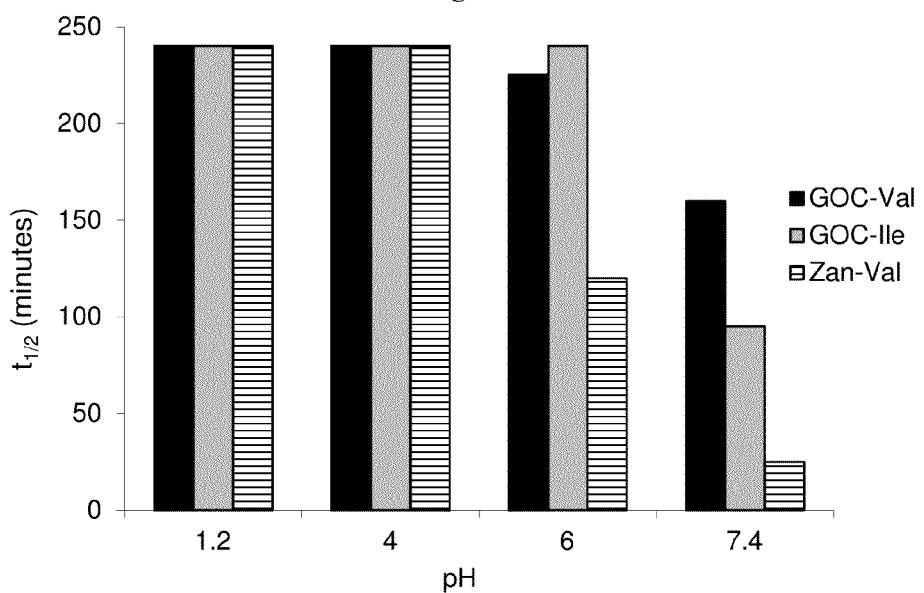
FIG. 1 is a bar graph showing the hydrolysis rate over the pH range 1.2-7.4 at 37° C. for prodrugs of the present invention valine ethoxyester of zanamivir (Zan-Val, the valine ethoxyester of guanidine oseltamivir (GOC-Val) and the isoleucine ethoxyester of guanidine oseltamivir (GOC-Ile)

Prodrugs of neuraminidase inhibitors are provided according to the present invention which have the general formula (I):

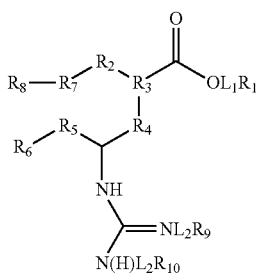

(I)

where $R_1$ is an amino acid residue having the formula $—C(O)CH(R')NH_2$, a dipeptide residue having the formula $—C(O)(CH_2)_nCH(R')N(H)C(O)(CH_2)_nCH(R'')NH_2$, a tripeptide residue having the formula $—C(O)(CH_2)_nCH(R')N(H)C(O)(CH_2)_nCH(R'')N(H)C(O)(CH_2)_nCH(R''')NH_2$, —H, $—COC(CH_3)_2CH_2R^*$, $—COCH_2CH_2R^*$ or $—COCH_3$; n is zero, one or two (corresponding to an α, β or γ amino acid, respectively); $R_2$ is a nullity or —CR*R**, —O or —CR*(OH); R* is —H, $—C_1$-$C_8$ alkyl, or $—C_1$-$C_6$ alkyl having a heteroatom substituent of hydroxyl, carboxyl, or primary amine; R** is R* or an electron of covalent bond; $R_3$ is an $sp^2$ hybridized C or CR*; $R_4$ is CR*R** when $R_3$ is CR* and an $sp^2$ hybridized C when $R_3$ is the $sp^2$ hybridized C forming an ethylenic unsaturation therebetween, $R_4$ is —CH; $R_5$ is —CR*R and R is the electron of a covalent bond when bonded to $R_2$ or $R_7$ to form a 5- or 6-member cyclic structure; $R_6$ is $—NH—C(O)—CH_2R^*$, $R_7$ is a nullity, —CR*R** and $R_8$ is $—CR^*(OR_{11})CR^*(OR_{12})CHR^*(OR_{13})$; $R_{11}$, $R_{12}$ and $R_{13}$ are each independently an amino acid residue having the formula $—C(O)(CH_2)_nCH(R')NH_2$, a dipeptide residue having the formula $—C(O)(CH_2)_nCH(R')N(H)C(O)(CH_2)_nCH(R'')NH_2$, a tripeptide residue having the formula $—C(O)(CH_2)_nCH(R')N(H)C(O)(CH_2)_nCH(R'')N(H)C(O)(CH_2)_nCH(R''')NH_2$, —H, $—COC(CH_3)_2CH_2R^*$, $—COCH_2CH_2R^*$, or $—COCH_3$; $R_9$ and $R_{10}$ are each independently an amino acid residue having the formula $—C(O)(CH_2)_nCH(R')NH_2$, a dipeptide residue having the formula $—C(O)(CH_2)_nCH(R')N(H)C(O)(CH_2)_nCH(R'')NH_2$, a tripeptide residue having the formula $—C(O)(CH_2)_nCH(R')N(H)C(O)(CH_2)_nCH(R'')N(H)C(O)CH(R''')NH_2$ or —H; $L_1$ is a nullity, $—[(CH_2)_nCH(CH_2R^*)O]_m$ or $—[(CH_2)_nCH_2O]_m$, with the proviso that $L_1$ is $—[(CH_2)_nCH(CH_2R^*)O]_m$ or $—[(CH_2)_nCH_2O]_m$ when $R_1$ is a single amino acid residue, a dipeptide residue or a tripeptide residue; m is 1; $L_2$ is a nullity, $—C(O)(CH_2)_nCH(CH_2R^*)O$ or $—C(O)O(CH_2)_nCH_2O$ with the proviso that $L_2$ is $—C(O)[(CH_2)_nCH(CH_2R^*)O]_m$ or $—C(O)O[(CH_2)_nCH_2O]_m$ when $R_9$ or $R_{10}$ is a single amino acid residue or a dipeptide residue; R', R'' and R''' are in each occurrence independently selected amino acid side chain; with the proviso that at least one of $R_1$, $R_9$, $R_{10}$, $R_{11}$, $R_{13}$ or $R_{13}$ is a single α, β or γ amino acid residue, a dipeptide residue or a tripeptide residue. In a specific preferred embodiment of the prodrug of formula (I) n is zero in each occurrence and R* is H in each occurrence.

With respect to the formulae used herein a parenthetical group is bonded to the immediately preceding non-hydrogen atom and not to the immediately succeeding non-hydrogen atom. This convention as to the use of parenthetical groups does not apply when the parenthetical group is immediately succeeded by a subscript of n.

Prodrugs of neuraminidase inhibitors represented by formula I are characterized by modified uptake into cells expressing an amino acid or peptide transporter compared to a corresponding unmodified neuraminidase inhibitor. It is appreciated that through selection of the various variable groups in formula I active uptake to an inventive prodrug is enhanced, bioavailability increased, or a combination thereof. It is also appreciated that often in instance when a prodrug of formula I is optimized for enhanced active transport into a cell expressing a suitable peptide or amino acid transporter, this transport optimization is at the expense of a degree of bioavailability of the base drug.

Amino acid and peptide transporters and identification of cells having amino acid and peptide transporter activity are known in the art. For example, PEPT1 and/or PEPT2 are known transporters as described in references [29]-[36]. Neuraminidase amino acid prodrugs with alkoxy moieties intermediate between the base drug carbonyl carbon and the α, β or γ amino acid have been discovered that are surprisingly effective for modifying cellular transport and bioavailability relative to the base drug and often providing an increase in both cellular transport and bioavailability.

Prodrugs of neuraminidase inhibitors represented by formula I are cleaved by enzymatic and/or non-enzymatic mechanisms to produce the active neuraminidase inhibitor. For example, prodrugs of the present invention are hydrolyzed by hydrolytic enzymes. In a particular example, prodrugs of the present invention are hydrolyzed by valacyclovirase, an alpha-amino acid ester hydrolase described in reference [11].

Prodrugs of the present invention are cleaved by proteolytic enzymes in particular embodiments. Such proteolytic enzymes are proteases endogenous to a subject treated with a prodrug, or can be viral proteases, such as an influenza virus protease or an HCMV protease.

In particular embodiments of the present invention, prodrugs of the neuraminidase inhibitors zanamivir, oseltamivir and peramivir and neuraminidase inhibitor analogs of these drugs are provided.

Prodrugs of Zanamivir

Zanamivir has been shown to be a potent inhibitor of both influenza A and influenza B and of emerging resistant strains [63]. However, the low absolute oral availability of zanamivir ~2% [43], precludes oral administration.

Prodrugs of zanamivir are provided which include modified carboxyl, hydroxyl, and/or guanidine functional groups compared to the parent compound.

For reference, the parent compound zanamivir (II) is shown:

(II)

In particular embodiments of inventive prodrugs, a carboxyl, a hydroxyl, and/or a guanidine functional group of the parent compound zanamivir is modified to include a carbonyl ester alkoxy amino acid, a carbonyl ester alkoxy dipeptide or a carbonyl ester alkoxy tripeptide of the zanamivir carboxylic acid group; a carbonyl alkoxy amino acid, a carbonyl alkoxy dipeptide or a carbonyl alkoxy tripeptide on the zanamivir guanidyl group; and/or an amino acid ester, dipeptide ester and/or tripeptide ester at one or more primary alcohol sites of a zanamivir.

In preferred embodiments of inventive prodrugs, carboxyl, hydroxyl, and/or guanidyl functional group of the parent compound zanamivir is modified to include a carbonyl ester ethoxy amino acid, a carbonyl ester ethoxy dipeptide or a carbonyl ester ethoxy tripeptide derived from the carboxyl; a carbonyl ethoxy amino acid, a carbonyl ethoxy dipeptide and/or a carbonyl ethoxy tripeptide derived from the guanidyl; and/or an amino acid, dipeptide ester and/or tripeptide ester at one or more primary alcohol sites of the parent compound. In this context, "ethoxy" refers to total number of carbons in the linkage (e.g., 2 carbons for ethoxy linkage $[(CH_3)HC(OR_1)(OR_2)]$—the "oxy" refers to the single carbon atom attached to two oxygens (it is at the oxidation state of a carbonyl). Accordingly, the prodrugs have methyl-methoxy and not ethoxy groups intermediate between core therapeutic and amino acid.

Zanamivir prodrugs according to embodiments of the present invention are represented by formula (III):

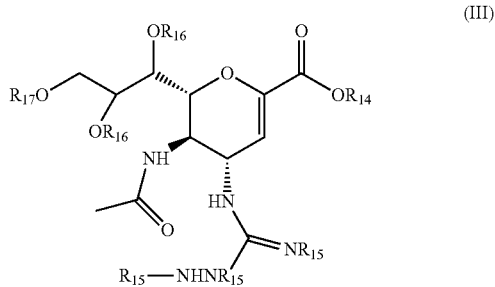

(III)

where $R_{14}$ is —CH(CH$_3$)OC(O)(CH$_2$)$_n$CH(R') NH$_2$, —CH(CH$_3$)OC(O)(CH$_2$)$_n$CH(R')N(H)C(O)(CH$_2$)$_n$CH(R") NH$_2$, —CH(CH$_3$)OC(O)(CH$_2$)$_n$CH(R')N(H)C(O)(CH$_2$)$_n$CH(R") N(H)C(O)(CH$_2$)$_n$CH(R''')NH$_2$, —H, —COC(CH$_3$)$_2$CH$_2$R*, —COCH$_2$CH$_2$R*, or —COCH$_3$; n is zero or one; R* is —H, —C$_1$-C$_8$ alkyl, or —C$_1$-C$_6$ alkyl having a heteroatom substituent of hydroxyl, carboxyl, or primary amine; $R_{15}$ is in each occurrence independently —C(O)OCH(CH$_3$)OC(O) (CH$_2$)$_n$CH(R')NH$_2$, —C(O)OCH(CH$_3$)OC(O) (CH$_2$)$_n$CH(R')N(H)C(O)(CH$_2$)$_n$CH(R-)NH$_2$, —CH(CH$_3$)O—C(O) (CH$_2$)$_n$CH(R')N(H)C(O) (CH$_2$)$_n$CH(R")N(H)C(O)(CH$_2$)$_n$ CH(R''')NH$_2$, —H, —COC(CH$_3$)$_2$CH$_2$R*, —COCH$_2$ CH$_2$R*, or —COCH$_3$; $R_{16}$ and $R_{17}$ are each independently —H, an amino acid residue having the formula C(O) (CH$_2$)$_n$ CH(R')NH$_2$, a dipeptide residue having the formula C(O) (CH$_2$)$_n$CH(R')N(H)C(O) (CH$_2$)$_n$CH(R")NH$_2$, or a tripeptide residue —CH(CH$_3$)O—C(O)(CH$_2$)$_n$CH(R')N(H)C(O) (CH$_2$)$_n$ CH(R")N(H)C(O)(CH$_2$)$_n$CH(R''')NH$_2$, where R', R" and R''' are each an independently selected amino acid side chain; and where at least one of $R_{14}$, $R_{15}$, $R_{16}$ and $R_{17}$ includes an amino acid, dipeptide or tripeptide residue.

In specific embodiments, zanavimir prodrugs of the present invention include zanamivir ethoxyvaline ester, zanamivir ethoxyleucine ester, zanamivir ethoxyisoleucine ester and zanamivir ethoxyphenylalanine ester. Again, "ethoxy" refers to total number of carbons in the linkage (e.g., 2 carbons for ethoxy linkage $[(CH_3)HC(OR1)(OR2)]$—the "oxy" refers to the single carbon atom attached to two oxygens (it is at the oxidation state of a carbonyl).

Prodrugs of Oseltamivir and Oseltamivir Analogs

Oseltamivir carboxylate is a potent transition state analog inhibitor of influenza virus neuraminidase (IC$_{50}$=2 nM). The guanidine analog of oseltamivir carboxylate is an approximately 2-fold more potent inhibitor in vitro (IC$_{50}$=0.9 nM) but is 10 times more potent in tissue culture of influenza virus replication. However, both oseltamivir carboxylate and the guanidine analog of oseltamivir carboxylate are poorly bioavailable (~4.0%). Compound IV, oseltamivir, the ethyl ester analog of oseltamivir carboxylate exhibited good oral bioavailability (11-73%) in rats, mice, dogs and ferrets [21]. However, the ethyl ester prodrug of the more potent guanidine analog, compound V, did not exhibit enhancement in oral bioavailability (~2%).

Prodrugs of oseltamivir and a guanidine analog of oseltamivir are provided according to embodiments of the present invention.

For reference, the base drug oseltamivir (IV) is shown along with the guanidine analog of oseltamivir (V):

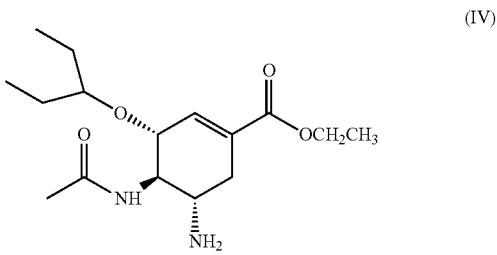

(IV)

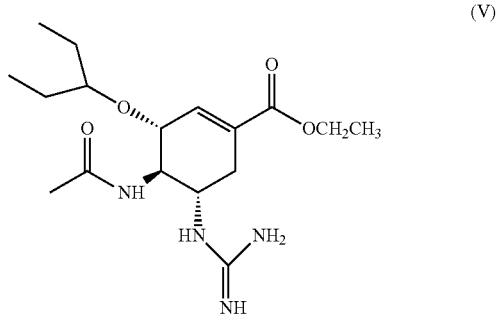

(V)

Prodrugs of oseltamivir carboxylate and guanidine analogs of oseltamivir carboxylate are provided which include a modified carboxyl and/or guanidine functional group compared to the parent compounds such that one or more ethoxy esters of an amino acid, dipeptide and/or tripeptide is present at the carboxyl and/or guanidine functionalities.

In particular embodiments of inventive prodrugs, the ester and/or guanidyl functional groups of the base compounds is modified to include an alkoxy amino acid ester, an alkoxy dipeptide ester or an alkoxy tripeptide ester in place of the ethyl ester of formulae IV or V; and/or a carbonyl alkoxy amino acid, a carbonyl alkoxy dipeptide or a carbonyl alkoxy tripeptide on the guanidyl group in formula V.

In preferred embodiments of inventive prodrugs, the carboxyl and/or guanidyl functional group of the parent compound oseltamivir carboxylate or oseltamivir carboxylate guanidine analog is modified to include a carbonyl ethoxy amino acid, a carbonyl ethoxy dipeptide or a carbonyl ethoxy tripeptide on the carboxyl; and/or a carbonyl ethoxy amino acid, a carbonyl ethoxy dipeptide or a carbonyl ethoxy tripeptide on the guanidine group of the parent compound.

Prodrugs of oseltamivir carboxylate according to embodiments of the present invention are represented by formula (VI):

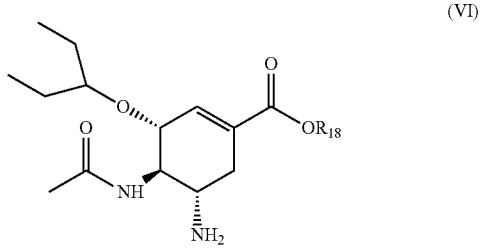

(VI)

where $R_{18}$ is —CH(CH$_3$)OC(O)(CH$_2$)$_n$CH(R')NH$_2$, —CH(CH$_3$)OC(O)(CH$_2$)$_n$CH(R')N(H)C(O)(CH$_2$)$_n$CH(R")NH$_2$, —CH(CH$_3$)OC(O)(CH$_2$)$_n$CH(R')N(H)C(O)(CH$_2$)$_n$CH(R") N(H)C(O)(CH$_2$)$_n$CH(R''')NH$_2$, —COC(CH$_3$)$_2$CH$_2$R*, —COCH$_2$CH$_2$R*, or —COCH$_3$; n is zero or one; R* is —H, —C$_1$-C$_8$ alkyl, or —C$_1$-C$_6$ alkyl having a heteroatom substituent of hydroxyl, carboxyl, or primary amine; and R', R" and R''' are each independently an amino acid side chain.

In specific embodiments, oseltamivir carboxylate prodrugs of the present invention include oseltamivir carboxylate ethoxyvaline ester, oseltamivir carboxylate ethoxyleucine ester, oseltamivir carboxylate ethoxyisoleucine ester and oseltamivir carboxylate ethoxyphenylalanine ester.

Prodrugs of a guanidine analog (V) of oseltamivir carboxylate according to embodiments of the present invention are represented by formula (VII):

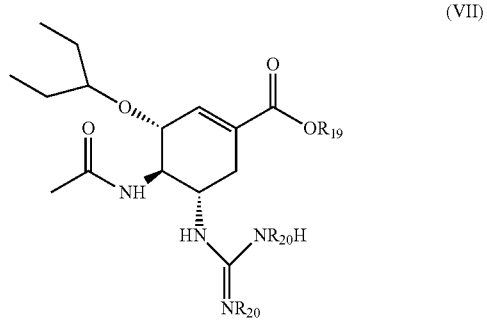

(VII)

where $R_{10}$ is —CH(CH$_3$)OC(O)(CH$_2$)$_n$CH(R')NH$_2$, —CH(CH$_3$)OC(O)(CH$_2$)$_n$CH(R')N(H)C(O)(CH$_2$)$_n$CH(R")NH$_2$, —CH(CH$_3$)OC(O)(CH$_2$)$_n$CH(R')N(H)C(O)(CH$_2$)$_n$CH(R") N(H)C(O)(CH$_2$)$_n$CH(R''')NH$_2$, —H, —COC(CH$_3$)$_2$CH$_2$R*, —COCH$_2$CH$_2$R*, or —COCH$_3$; n is zero or one; R* is —H, —C$_1$-C$_8$ alkyl, or —C$_1$-C$_6$ alkyl having a heteroatom substituent of hydroxyl, carboxyl, or primary amine; $R_{20}$ is in each occurrence independently —CH(CH$_3$)OC(O)(CH$_2$)$_n$CH(R')NH$_2$, —CH(CH$_3$)OC(O)(CH$_2$)$_n$CH(R')N(H)C(O)(CH$_2$)$_n$CH(R''')NH$_2$, —CH(CH$_3$)OC(O)(CH$_2$)$_n$CH(R')N(H)C(O)(CH$_2$)$_n$CH(R")N(H)C(O)(CH$_2$)$_n$CH(R''')NH$_2$, or —H; R', R" and R''' are each an independently an amino acid side chain; and where at least one $R_{10}$ or $R_{20}$ includes an amino acid residue, dipeptide residue or tripeptide residue.

Prodrugs of oseltamivir carboxylate and guanidine analogs of oseltamivir carboxylate according to the present invention are actively transported across cell barriers by endogenous transporters and the prodrug is hydrolyzed enzymatically and/or non-enzymatically to yield the active metabolite of oseltamivir and/or guanidine oseltamivir. The prodrugs are characterized by enhanced bioavailability compared to oseltamivir carboxylate and the guanidine analog of oseltamivir carboxylate.

In specific embodiments, guanidine oseltamivir prodrugs of the present invention include oseltamivir guanidino ethoxyvaline ester, oseltamivir guanidino ethoxyleucine ester, oseltamivir guanidino ethoxyisoleucine ester and oseltamivir guanidino ethoxyphenylalanine ester.

Peramivir Prodrugs

Peramivir is a cyclopentane neuraminidase inhibitor that exhibits in vitro and in vivo activity against various influenza A and B viruses including the highly pathogenic H5N1 viruses [99-102]. Peramivir has demonstrated a good safety profile when tested in mice, rats, primates and dogs, following oral, intravenous and intramuscular administration [103]. However peramivir failed to achieve significant clinical effects in phase 2 and phase 3 clinical trials owing to its low oral bioavailability (≤3%) [103].

Prodrugs of peramivir having enhanced bioavailability compared to the parent compound are provided according to embodiments of the present invention.

For reference, the base compound peramivir (VIII) is shown:

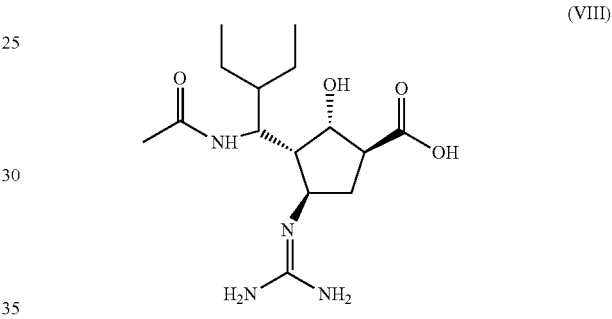

(VIII)

Prodrugs of peramivir are provided which include a modified carboxyl and/or guanidine functional group compared to the parent compound such that one or more ethoxy esters of amino acids and/or dipeptides is present at the carboxyl and/or guanidyl functionalities.

In particular embodiments of inventive prodrugs, the carboxyl and/or guanidyl functional group of the parent compound peramivir is modified to include a carbonyl ethoxy amino acid or a carbonyl ethoxy dipeptide on the carboxyl; and/or a carbonyl ethoxy amino acid and/or a carbonyl ethoxy dipeptide on the guanidine.

Prodrugs of peramivir according to embodiments of the present invention are represented by formula (IX):

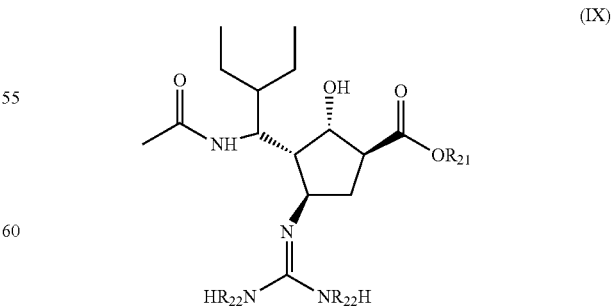

(IX)

where $R_{21}$ is —CH(CH$_3$)OC(O)(CH$_2$)$_n$CH(R')NH$_2$, —CH(CH$_3$)OC(O)(CH$_2$)$_n$CH(R')N(H)C(O)(CH$_2$)$_n$CH(R")NH$_2$, —CH(CH$_3$)OC(O)(CH$_2$)$_n$CH(R')N(H)C(O)(CH$_2$)$_n$CH(R")

N(H)C(O)(CH$_2$)$_n$CH(R''')NH$_2$, —H, —COC(CH$_3$)$_2$CH$_2$R*, —COCH$_2$CH$_2$R*, or —COCH$_3$; n is zero or one; R* is —H, —C$_1$-C$_8$ alkyl, or —C$_1$-C$_6$ alkyl having a heteroatom substituent of hydroxyl, carboxyl, or primary amine; R$_{22}$ is in each occurrence independently —CH(CH$_3$)OC(O)(CH$_2$)$_n$CH(R')NH$_2$, —CH(CH$_3$)OC(O)(CH$_2$)$_n$CH(R')N(H)C(O)(CH$_2$)$_n$CH(R'')NH$_2$, —CH(CH$_3$)OC(O)(CH$_2$)$_n$CH(R')N(H)C(O)(CH$_2$)$_n$CH(R'')N(H)C(O)(CH$_2$)$_n$CH(R''')NH$_2$, or —H; R', R'' and R''' are each an independently selected amino acid side chain; and where at least one R$_{21}$ or R$_{22}$ includes an amino acid residue, dipeptide residue or tripeptide residue.

In specific embodiments, peramivir prodrugs of the present invention include peramivir ethoxyvaline ester, peramivir ethoxyleucine ester, peramivir ethoxyisoleucine ester and peramivir ethoxyphenylalanine ester.

In further specific embodiments, peramivir prodrugs of the present invention include peramivir guanidino ethoxyvaline ester, peramivir guanidino ethoxyleucine ester, peramivir guanidino ethoxyisoleucine ester and peramivir guanidino ethoxyphenylalanine ester.

In preferred embodiments, modification of a parent compound to produce a prodrug of the present invention enhances bioavailability of the parent compound and/or a bioactive form of the parent compound by greater than 2 fold.

Naturally occurring or non-naturally occurring amino acids are used to prepare the prodrugs of the invention. In particular, standard amino acids suitable as a prodrug moiety include valine, leucine, isoleucine, methionine, phenylalanine, asparagine, glutamic acid, glutamine, histidine, lysine, arginine, aspartic acid, glycine, alanine, serine, threonine, tyrosine, tryptophan, cysteine, and proline. Particularly preferred are L-amino acids. Without intending to be bound to a particular theory, naturally occurring amino acids are believed to facilitate active prodrug transportation in cells expressing amino acid or peptide transporters, such as those detailed herein. L-amino acids are also appreciated to be more often be kinetically faster cleavage substrates for autologous subject enzymes. As a result, D-amino acids generally are more slowly cleaved by autologous subject enzymes while tending to be more slowly driven in active cellular transport. Also, naturally occurring, non-standard amino acids are operative in the compositions and methods of the invention. For example, in addition to the standard naturally occurring amino acids commonly found in proteins, naturally occurring amino acids also illustratively include 4-hydroxyproline, γ-carboxyglutamic acid, selenocysteine, desmosine, 6-N-methyllysine, ε-N,N,N-trimethyllysine, 3-methylhistidine, O-phosphoserine, 5-hydroxylysine, ε-N-acetyllysine, ω-N-methylarginine, N-acetylserine, γ-aminobutyric acid, citrulline, ornithine, azaserine, homocysteine, β-cyanoalanine and S-adenosylmethionine. Non-naturally occurring amino acids include phenyl glycine, meta-tyrosine, para-amino phenylalanine, 3-(3-pyridyl)-L-alanine, 4-(trifluoromethyl)-D-phenylalanine, and the like.

In one embodiment of an inventive compound, an amino acid covalently coupled to the neuraminidase inhibitor is a non-polar amino acid such as valine, phenylalanine, leucine, isoleucine, glycine, alanine and methionine. In particular embodiments, an amino acid covalently coupled to the neuraminidase inhibitor has an aliphatic amino acid such as valine, phenylalanine, leucine and isoleucine. Without intending to be bound to a particular theory, aliphatic amino acids are believed to facilitate active prodrug transportation in cells expressing amino acid or peptide transporters. Preferably, all the amino acid side chains in an inventive prodrug are aliphatic.

Amino acid side chains are well known in the art, for example, as described in J. M. Berg et al., Biochemistry, W.H. Freeman; 6th ed., 2006; and D. L. Nelson et al., Lehninger Principles of Biochemistry, 4th ed., W.H. Freeman, 2004.

It is appreciated that prodrugs according to the present invention are useful to treat a variety of diseases responsive to neuraminidase inhibition. In particular, methods of treating viral infection using prodrugs of neuraminidase inhibitors are provided by the present invention. Illustratively, infection by influenza A virus and/or influenza B virus are treated using prodrugs of neuraminidase inhibitors.

In a preferred embodiment, an inventive prodrug is formulated for administration to a human individual. However, it is appreciated that an inventive prodrug and method of treatment may be indicated in non-human applications as well. Thus, an inventive prodrug is advantageously administered to a non-human organism such as a rodent, porcine, bovine, equine, avian, canine, feline or other such species wherein the organism possesses a membrane transporter for which the prodrug is a substrate and an enzyme active to hydrolyze the prodrug.

A method of treatment according to the present invention includes administering an inventive prodrug to an organism possessing a membrane transporter for which the prodrug is a substrate and an enzyme active to hydrolyze the prodrug.

In a particular embodiment of an inventive method for delivering a pharmaceutical species to an individual the method includes the step of administering an inventive prodrug as described herein to the gastrointestinal lumen of an individual. The prodrug is transported from the gastrointestinal lumen by a specific transporter, enzymatically cleaved to yield an intermediate, and the intermediate is hydrolyzed non-enzymatically to yield the neuraminidase inhibitor, thereby delivering the neuraminidase inhibitor to the individual. It is appreciated that through selection of prodrug functionalities the cellular transport, half life of the prodrug and bioavailability of the base drug are readily controlled. These factors of prodrug functionality include, among others: amino acid side chain identity, side chain optical isomer, the total number of amino acid residues in the prodrug, the length of the alkyloxy linker, and the identity of the alkoxy linker.

Variable dosing regimens are operative in methods of treatment of the present invention. While single dose treatment is effective in producing therapeutic effects, it is noted that longer courses of treatment such as several days to weeks. While dosimetry for a given inventive prodrug will vary, dosimetry will depend on factors illustratively including target cell mass, effective active species X cellular concentration, transporter efficiency, systemic prodrug degradation kinetics, and secondary enzymatic cleavage that reduces active species lifetime. It is appreciated that conventional systemic dosimetry is not applicable to the present invention.

A prodrug is administered by a route determined to be appropriate for a particular subject by one skilled in the art. For example, the prodrug is administered orally; parentally, such as intravenously; by intramuscular injection; by intraperitoneal injection; intratumorally; transdermally; or rectally. The exact dose of prodrug required is appreciated to vary from subject to subject, depending on the age, weight and general condition of the subject, the severity of the disease being treated, the particular pharmaceutical species, the mode of administration, and the like. An appropriate dose is readily determined by one of ordinary skill in the art using only routine experimentation given the teachings herein. Generally, dosage is in the range of about 0.5-500 mg per m2.

Depending on the intended mode of administration, the prodrug can be in pharmaceutical compositions in the form of solid, semi-solid or liquid dosage forms, such as, for example, tablets, suppositories, pills, capsules, powders, liquids, or suspensions, preferably in unit dosage form suitable for single administration of a precise dosage. Time release preparations are specifically contemplated as effective dosage formulations. The compositions will include an effective amount of the selected substrate in combination with a pharmaceutically acceptable carrier and, in addition, may include other medicinal agents, pharmaceutical agents, carriers, or diluents. Further, a prodrug may be formulated as a pharmaceutically acceptable salt.

For solid compositions, conventional nontoxic solid carriers include, for example, pharmaceutical grades of mannitol, lactose, starch, magnesium stearate, sodium saccharine, talc, cellulose, glucose, sucrose and magnesium carbonate. Liquid pharmaceutically administrable compositions can, for example, be prepared by dissolving or dispersing an active compound with optimal pharmaceutical adjuvants in an excipient, such as water, saline, aqueous dextrose, glycerol, or ethanol, to thereby form a solution or suspension. If desired, the pharmaceutical composition to be administered may also contain minor amounts of nontoxic auxiliary substances such as wetting or emulsifying agents, pH buffering agents, for example, sodium acetate or triethanolamine oleate. Actual methods of preparing such dosage forms are known, or will be apparent, to those skilled in this art; for example, see Remington's The Science and Practice of Pharmacy, 21st Edition, Lippincott Williams & Wilkins, 2005.

For oral administration, fine powders or granules may contain diluting, dispersing, and/or surface active agents, and may be presented in water or in a syrup, in capsules or sachets in the dry state or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. Tablets and granules are preferred oral administration forms, and these may be coated.

Parenteral administration is generally by injection. Injectables can be prepared in conventional forms, either liquid solutions or suspensions, solid forms suitable for solution or prior to injection, or as suspension in liquid prior to injection or as emulsions.

Embodiments of inventive compositions and methods are illustrated in the following examples. These examples are provided for illustrative purposes and are not considered limitations on the scope of inventive compositions and methods.

EXAMPLES

Example 1

Parent compounds, such as zanamivir can be purchased commercially or synthesized.

The synthesis of zanamivir is shown in Scheme 1. The starting material used for zanamivir synthesis is sialic acid 1, which was converted to the methyl ester 2, in presence of Dowex H+ as described in detail in reference 104. The hydroxyl groups of 2 are protected with acetyl groups to give compound 3, which was then converted to the oxazoline derivative 4 in the presence of trimethyltrifluoromethanesulfonate as described in detail in reference 105. Azide 5 was synthesized from 4 in presence of azidotrimethylsilane as described in detail in reference 105. The azide is reduced to the corresponding amine 6 by using Lindlar's catalyst, and the amine is in turn converted to the guanidine derivative 7 as described in detail in reference 106. The final step involves the deprotection of the methyl ester and acetyl groups in the presence of methanolic sodium hydroxide to give Boc-protected zanamivir 8 as described in detail in reference 106. 8, $^1$H NMR (CD$_3$OD) δ (ppm) 5.6 (d, J=2.0 Hz, 1H), 5.01 (dd, J=9.6, 2.1 Hz, 1H), 4.25 (dd, J=10.8, 1.1 Hz, 1H), 4.18 (dd, J=10.6, 9.6 Hz, 1H), 3.89 (ddd, J=9.4, 6.2, 2.7 Hz, 1H), 3.84 (dd, J=11.3, 2.8 Hz, 1H), 3.67 (dd, J=11.3, 5.8 Hz, 1H), 3.57 (d, J=9.3 Hz, 1H), 1.9 (s, 3H), 1.55 (s, 9H), 1.50 (s, 9H); ESI-MS: 533 (M+H)+.

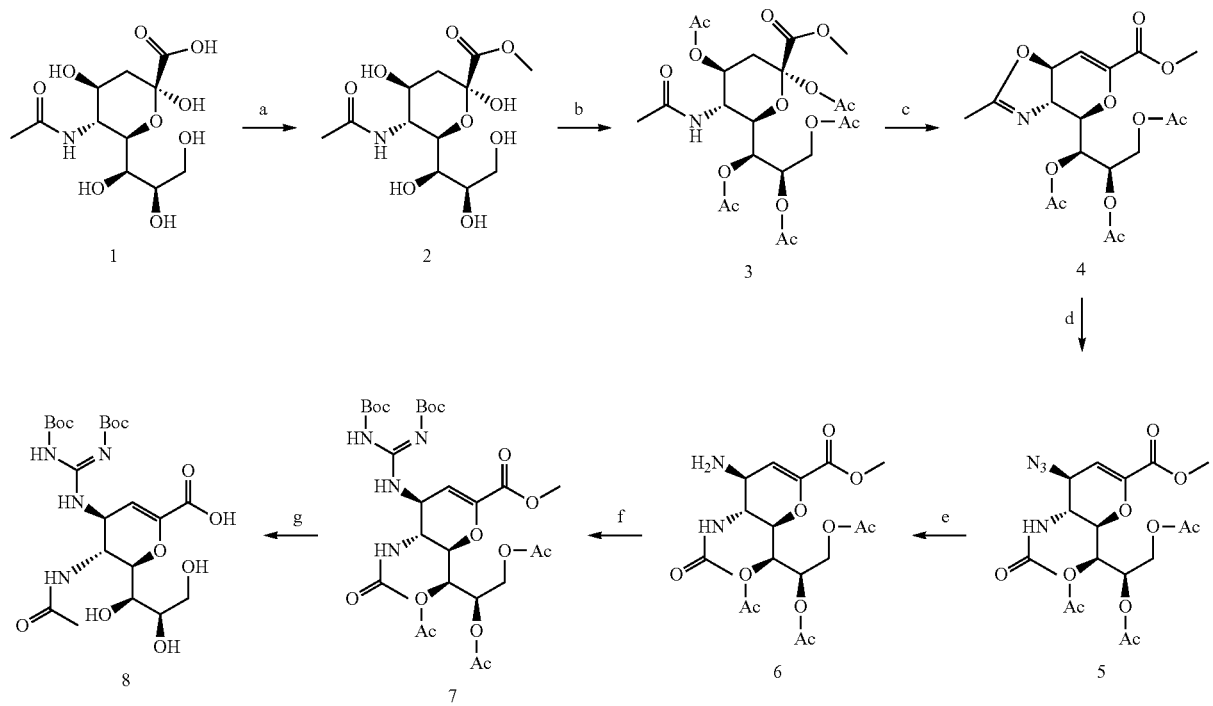

Scheme 1 a) Dowex H, Methanol B) Aceticanhydride, DMAP, pyridine c) trimethylsilyl trifluoromethane sulfonate, ethylacetate d) azidotrimethylsilane, butanol e) Lindlar's catalyst, ethanol f) N,N'-bis-tert-butoxycarbonyl-1H-pyrazole-1-carboxamidine, tetrahydrofuran g) sodium hydroxide, methanol

Example 2

Ethoxyester Derivatives of Zanamivir

Synthetic steps for ethoxyester derivatives of zanamivir are summarized in Scheme 2. Intermediate 10 was synthesized from intermediate 8 and α-chloro methylester of respective R group as described in detail in reference 107. The alkyl α-chloro methylester was synthesized from respective carbonyl chloride in the presence of zinc chloride and acetaldehyde as described in detail in reference 107. For the compounds with amino acid substitution instead of an alkyl group, the α-chloro methylester was synthesized from the cesium salt of respective Boc-protected amino acid in presence of 1-chloro-1-bromoethane as described in detail in reference 108. Compound 11 is synthesized from 10 using coupling conditions. The final step involves the deprotection of the Boc-protecting group to give final compounds 4 a-x. Zanamivir-Valine (Zan-Val), $^1$H NMR ($CD_3OD$) δ (ppm) 6.9 (q, 1H), 5.8 (d, J=2.0 Hz, 1H), 5.2 (m, 1H), 4.9 (m, 1H), 4.2 (m, 2H), 4.02 (m, 2H), 3.9 (m, 1H), 3.7 (m, 1H), 2.14 (m, 1H), 2.08 (s, 3H), 2.01 (s, 3H), 0.98 (d, J=6.8 Hz, 3H), 0.90 (d, J=6.5 Hz, 3H); ESI-MS: 476 (M+H)+. The synthesis is also functional in the β and γ amino acid analogs of Val, Ile, Leu and Phe with comparable yields to those detailed above. D-alanine, α-amino acid, D-methionine α-amino acid and L-phenyl glycine are also prepared in good yield.

Example 3

Amino Acid Ester Prodrugs of Zanamivir

L-valine, L-leucine, L-isoleucine and L-phenylalanine ester prodrugs of zanamivir, shown below, are synthesized. For comparison, the free carboxylic group of zanamivir is esterified with an ethyl group initially, and the effect of the higher alcohol esters on the permeability properties is determined. The synthesis is also functional in the β and γ amino acid analogs of Val, Ile, Leu and Phe with comparable yields to those detailed above. D-alanine, α-amino acid, D-methionine α-amino acid and L-phenyl glycine are also prepared in good yield.

14 a-p

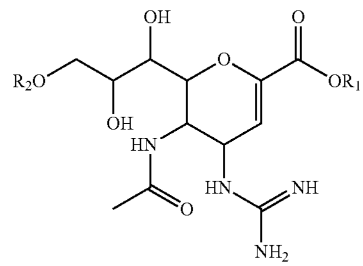

Scheme 2

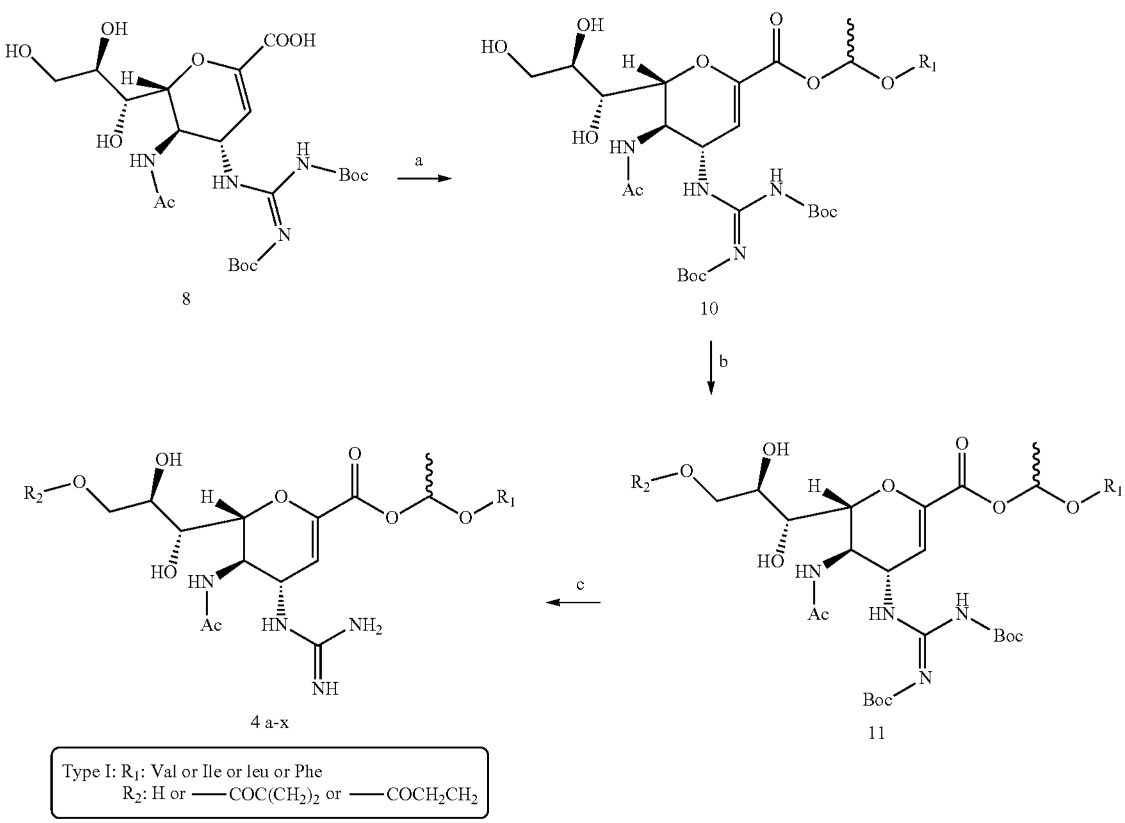

8

10

11

4 a-x

Type I: $R_1$: Val or Ile or leu or Phe
$R_2$: H or $-COC(CH_2)_2$ or $-COCH_2CH_2$ Type II: $R_1$: $-COC(CH_2)_2$ or $-COCH_2CH_2$ or $-COCH_2$
$R_2$: Val or Ile or leu or Phe a) R$-COCH(CH_2)Cl$ Triethylamine, dichloromethane b) $R_2OH$, EDC, DMAP, dichloromethane c) Trfluoracetice acid, Dichloromethane -continued

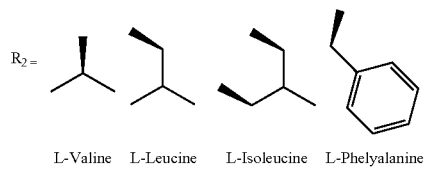

L-Valine L-Leucine L-Isoleucine L-Phelyalanine

Example 4
Synthesis of Ethoxy Amino Acid Esters of Guanidine Oseltamivir
The synthetic scheme for ethoxy amino acid esters of guanidine oseltamivir is shown in Scheme 3.

Ethoxy amino acid esters of guanidine oseltamivir, such as GOC-Val, are synthesized as per Scheme 3. Compound 2 is functionalized with a guanidino group by treatment with N,N'-bis(tert-butyloxycarbonyl)thiourea in the presence of mercury (II) chloride to yield 8 as described in detail in reference 109. Ethyl ester 8 is hydrolyzed using 1N LiOH in aqueous THF to yield free acid 9 as described in detail in reference 106. In a separate flask, cesium salts of Boc-protected amino acids (Boc-L-Val, Boc-L-Leu, Boc-L-Ile) are alkylated using 1-bromo-1-chloroethane and 1-bromo-2-chloroethane to afford 16 a-d as described in detail in reference 108. 16a-d are condensed with the free acid 9 as described in detail in reference 107 and further Boc-deprotected with trifluoro acetic acid to afford the final compounds 7a-d as described in detail in reference 106. GOC-Val, $^1H$ NMR ($CD_3OD$) δ (ppm) 0.87-1.03 (m, 12H), 1.49-1.54 (m, 6H), 1.80-1.84 (m, 4H), 1.94 (m, 1H), 2.10 (m, 1H), 3.16 (d, 1H, J=12.1), 3.37-3.41 (m, 1H), 3.78 (d, 1H, J=4.55), 4.05 (m, 1H), 4.17-4.25 (m, 1H), 5.00-5.02 (m, 1H), 6.55-6.61 (m, 1H)); ESI-MS: 470 (M+H)+.

Scheme 3

Example 5

Synthesis of Guanidino Prodrugs of Zanamivir

The guanidine functionality of zanamivir is modified to make guanidine amino acid prodrugs of zanamivir. A scheme for synthesis of guanidine derivatives is shown generally in Scheme 4.

Example 6

Synthesis of Guanidino Prodrugs of Guanidine Oseltamivir

The synthetic steps for guanidino prodrugs of guanidine oseltamivir are shown in Scheme 5.

Scheme 4

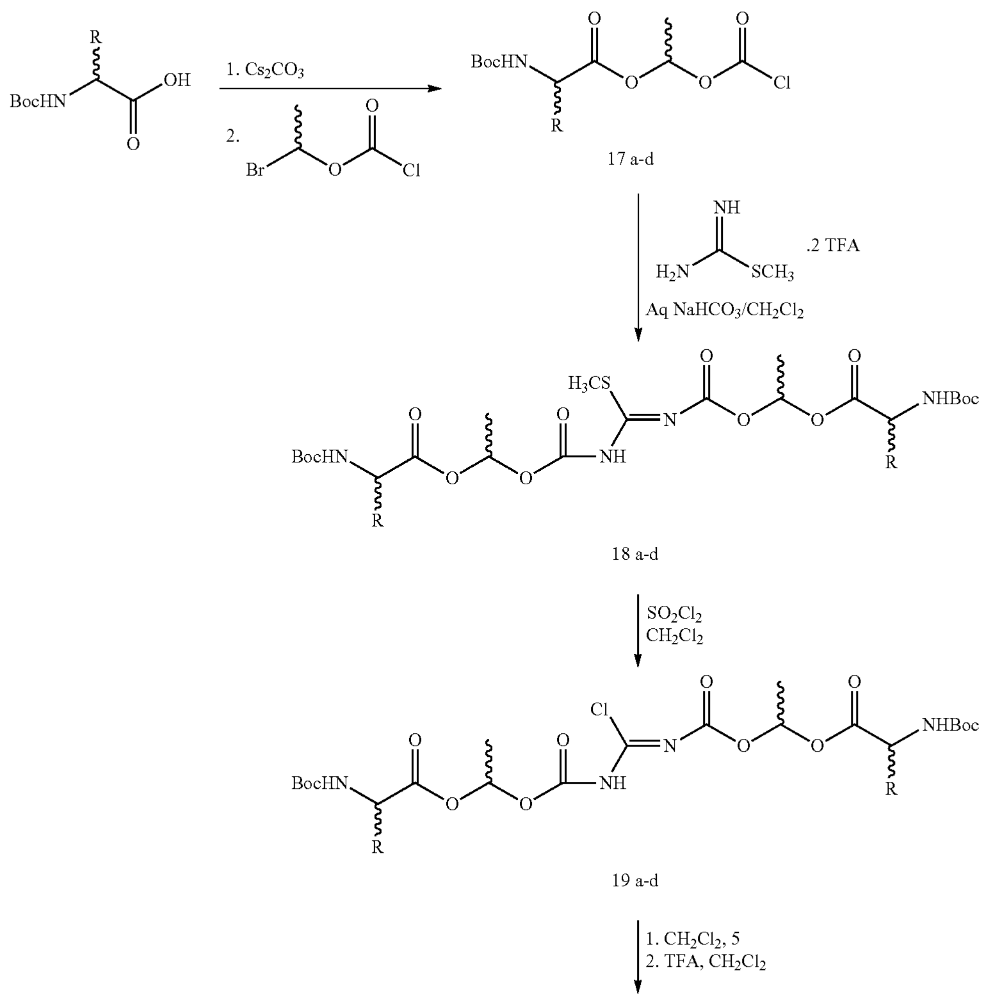

17 a-d 18 a-d 19 a-d 10 a-d

Analogs 10 a-d are synthesized as follows: Cesium salts of Boc-protected amino acids (Boc-L-Val, Boc-L-Leu, Boc-L-Ile, Boc-L-Phe) are alkylated using 1-bromoethyl chloroformate to obtain ethoxyethyl carbonochloridates 17a-d as described in detail in reference 108. A dichloromethane solution of 17a-d is stirred with saturated aqueous sodium bicarbonate solution of commercially available S-methylthiourea sulfate to give 18a-d as described in detail in reference 110. Reactive chloro intermediates 18a-d are obtained by reaction of 17a-d with sulfuryl chloride as described in detail in reference 110. These reactive intermediates are condensed with oseltamivir carboxylate at room temperature and subsequently Boc-deprotected to yield 10 a-d as guanidino prodrugs as described in detail in reference 110.

Example 7

Synthesis of Guanidino Prodrugs of Peramivir

Guanidino prodrugs of peramivir are synthesized generally as shown in Scheme 4.

The structures of particular L-valine, L-leucine, L-isoleucine and L-phenylalanine peramivir guanidino prodrugs are shown below. The synthesis is also functional in the β and γ amino acid analogs of Val, Ile, Leu and Phe with comparable yields to those detailed above. D-alanine, α-amino acid, D-methionine α-amino acid and L-phenyl glycine are also prepared in good yield.

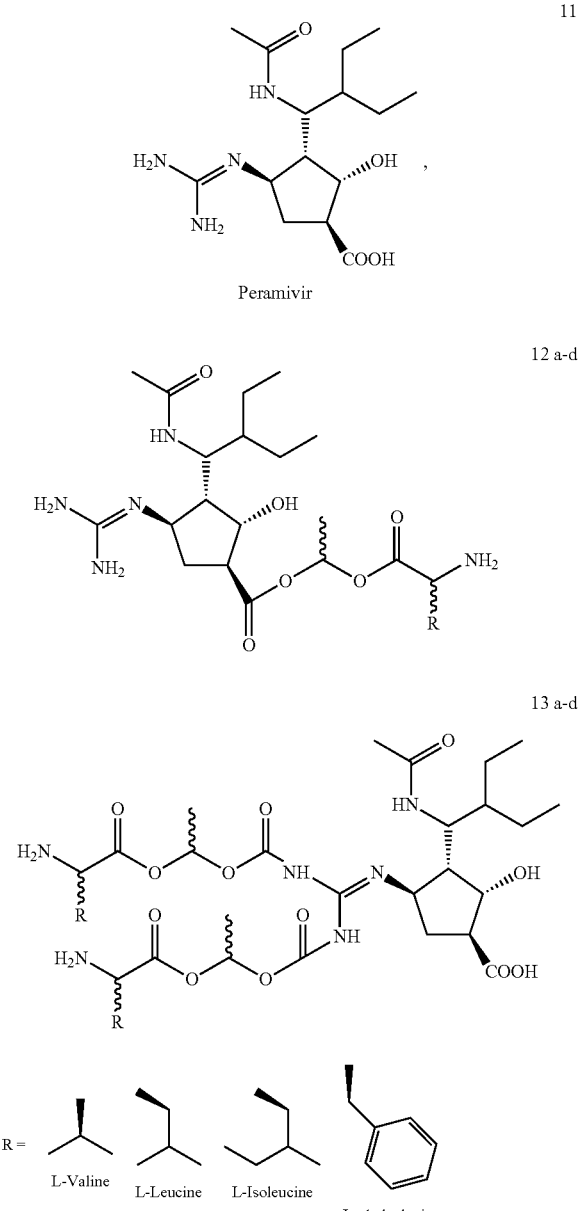

Scheme 5

Example 8

Activation of Prodrugs

The hydrolysis of prodrugs of the present invention in buffer was studied over the pH range 1.2-7.4 at 37° C. Results of analysis of the valine ethoxyester of zanamivir (Zan-Val, the valine ethoxyester of guanidine oseltamivir (GOC-Val) and the isoleucine ethoxyester of guanidine oseltamivir (GOC-11e) shown in FIG. 1. Zan-Val, GOC-Val, GOC-Ile show pH dependent hydrolysis. At pH >4, the prodrugs undergo base catalyzed hydrolysis leading to generation of the active metabolite and corresponding amino acid analog. The half-life is >4 hours at pH 4 and >2 hours at pH 5.5 (the pH of the upper small intestine). Prodrugs are more stable at lower pH (>>4 hours at pH 1.2). These results indicate that the prodrugs are sufficiently stable to be absorbed in the upper small intestine.

Example 9

Transport Inhibition and Uptake Results with Prodrugs

The affinity of zanamivir, GOC, 3-hydroxyphenylglycine (3-HPG) and prodrugs thereof for particular transporters is evaluated using [$^3$H]Gly-Sar uptake inhibition in Caco-2 cells and in HeLa/hPEPT1 cells. Valacyclovir, a known substrate of hPEPT1, was used as positive control (Table 1). Parent compounds Zanamivir, GOC, and 3-HPG exhibited poor affinity for the transporter in both Caco-2 cells and in HeLa/hPEPT1. The valyl and isoleucyl prodrugs of zanamivir, GOC, and 3-HPG have higher affinity for hPEPT1 than the parent compounds.

TABLE 1

$IC_{50}$ of [$^3$H]Gly-Sar uptake inhibition study in HeLa/hPEPT1 cells (mean ± sd, n = 2).

| Parent | $IC_{50}$ (mM) | Prodrug | $IC_{50}$ (mM) |
|---|---|---|---|
| GOC (6) | 6.6 ± 3.9 | GOC-Val (7a) | 0.19 ± 0.01 |
|  |  | GOC-Ile (7b) | 0.45 ± 0.18 |
| Zanamivir (3) | >30 | Zan-Val (4a) | 1.95 ± 0.19 |
|  |  | Zan-Ile (4b) | 3.04 ± 0.8 |
| 3-HPG (8a) | >5 | Val-3-HPG (9a) | 0.64 ± 0.09 |
|  |  | Ile-3-HPG (9b) | 0.57 ± 0.03 |
|  |  | Phe-3-HPG (9c) | 3.04 ± 0.49 |
| Valcyclovir | 1.88 ± 0.51 |  |  |

Figure 2:
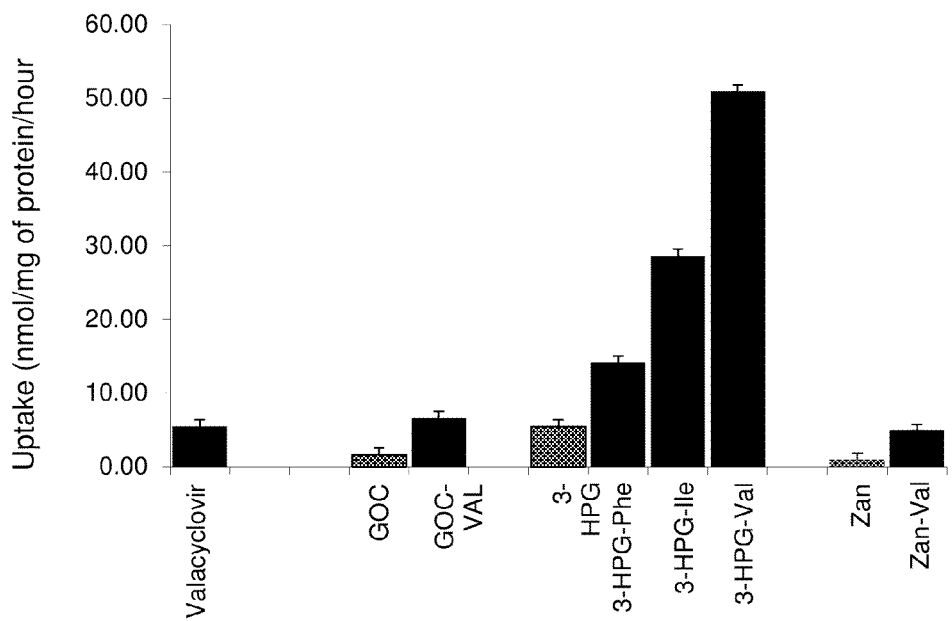
FIG. 2 is a bar graph showing the uptake for comparative, unmodified therapeutic agents and inventive prodrugs of GOC, 3-HPG and Zan in HeLa cells transfected to over express LPEPT1 transporter.

FIG. 2 shows prodrug uptake in HeLa cells transfected to overexpress hPEPT1. The prodrugs exhibited a 3- to 5-fold higher uptake in cells overexpressing hPEPT1 compared to the corresponding parent drug and up to 20-fold higher cells compared to control (control data not shown in the Figure). Good stability is observed in the donor compartment. Further, the parent drugs were the predominant species observed to be present in the cells incubated with the prodrugs, indicating rapid cellular hydrolysis of the prodrugs to yield the parent compounds.

Example 10

Jejunal Permeability

Figure 3:
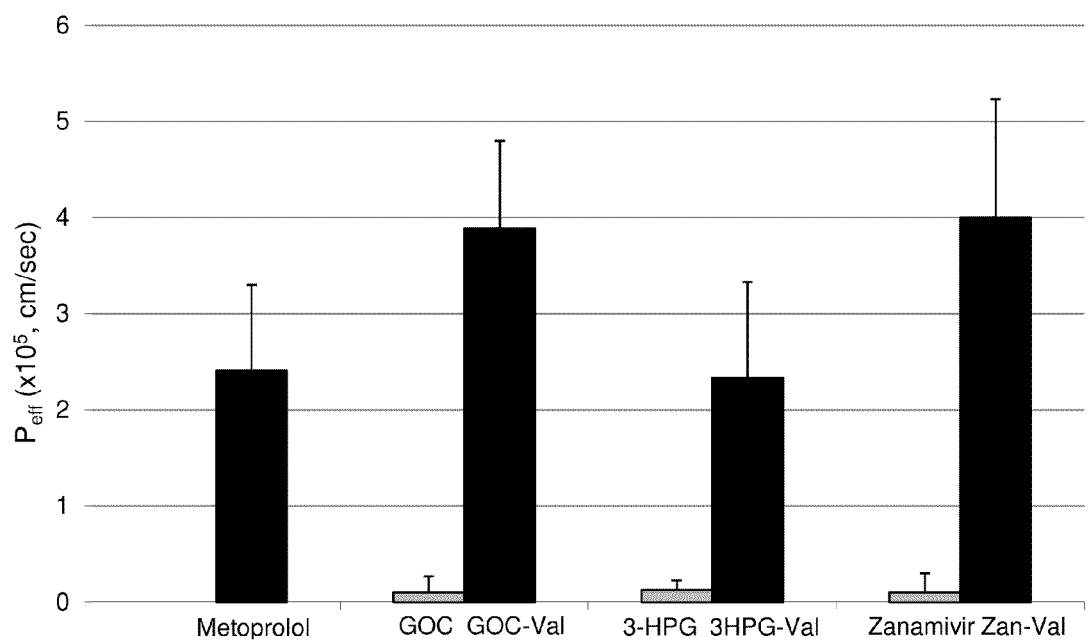
FIG. 3 is a bar graph showing permeability in rat perfused jejunum of inventive prodrugs Zan-Val, GOC-Val and 3-HPG-Ile compared to the unmodified therapeutic agents, metoprolol is also provided as a control showing the improved properties of inventive prodrugs.

Improved permeability of prodrugs Zan-Val, GOC-Val, and 3-HPG-Ile compared to the parent compounds is observed in the rat perfused jejunum, as shown in FIG. 3. As expected, the parent compounds, zanamivir, GOC, and 3-HPG, have a very low, essentially zero permeability in the jejunum, consistent with the known very low absorption. In contrast, the prodrugs, Zan-Val, GOC-Val and 3-HPG-Ile, show a high permeability, higher than that of metoprolol, a drug with >95% absorption.

These results demonstrate the transport and activation of the prodrugs of the present invention, improving the membrane permeability of the polar, poorly absorbed antiviral parent compounds.

Example 11

Testing for Activation of a Prodrug

Prodrugs of the present invention are tested for susceptibility to enzymatic hydrolysis using the prototype activation enzyme—VACVase. VACVase is isolated as described in Kim et al. (Kim I. et al., J Biol. Chem., 2003, 278(28):25348-56). A solution containing 1 mM of a prodrug compound is incubated with the VACVase enzyme at 25° C. The reaction is stopped by the addition of 5% trifluoroacetic acid and the amount of parent compound is determined by HPLC analysis.

Figure 4A:
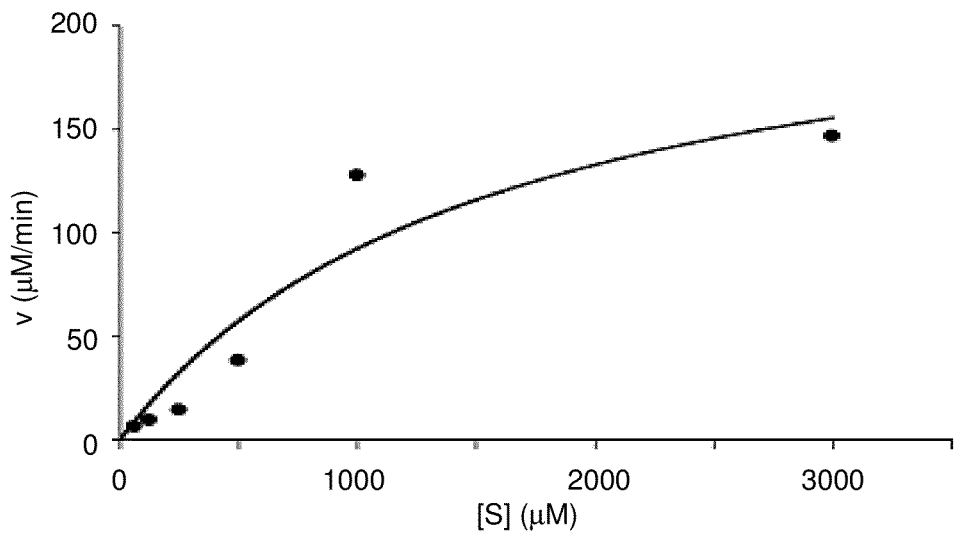
Figure 4B:
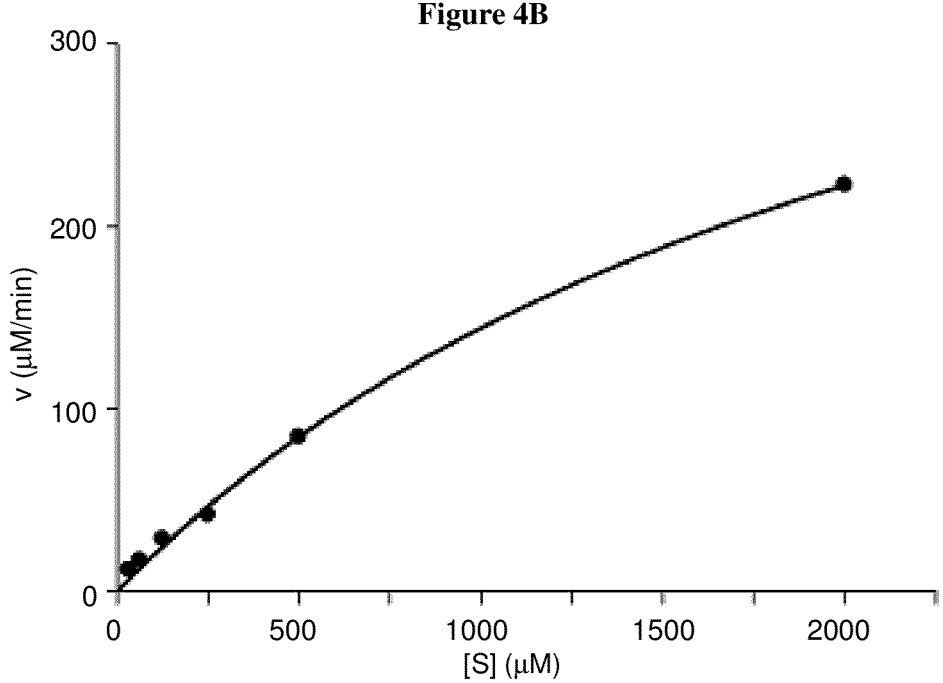

Results of analysis of hydrolysis of the prodrugs Zan-Val, GOC-Val, and the specific substrate (3-HPG-Val) by VACVase are shown in FIG. 4 and Table 2.

TABLE 2

|  | $K_m$ (mM) | $V_{max}$ (nmol/min/μg of VACVase) | $K_{cat}(s^{-1})$ | $K_{cat}/K_m$ $(mM^{-1}s^{-1})$ |
|---|---|---|---|---|
| Zan-Val | 1.55 | 47.2 | 21.2 | 13.7 |
| Goc-Val | 2.37 | 19.4 | 8.7 | 3.7 |
| 3-HPG-Val | 0.03 | 57.5 | 25.9 | 862 |
| VACV | 0.59 | 280 | 126 | 213 |

Example 12

Determination of Binding Affinity of Prodrugs for the Intestinal Peptide Transporter HPEPT1

Prodrugs are tested for their interaction with the transporter, HPEPT1, using tissue culture cells that are engineered to overexpress HPEPT1. In this example, the cells that overexpress HPEPT1, termed DC5, are a human meduloblastoma cell line that is stably transfected with a eukaryotic expression vector encoding HPEPT1. In this assay, the ability of the prodrug to competitively inhibit the uptake of a known substrate of HPEPT1 is measured. The known substrate is the dipeptide Glycine-Sarcosine (Gly-Sar) that has a radioactive label. DC5 cells are plated at a density of 12,000 cells/well in 96-well tissue culture plates and allowed to grow for 2 days. The cells are washed once with 200 microliters of uptake buffer and aspirated. The plates are cooled to 4° C. and 25 microliters of uptake buffer containing 125 nanomoles Gly-Sar (at a specific activity of 1 microcurie/micromole) is added. The uptake buffer also contains the prodrugs to be tested at concentrations ranging from 10 micromolar to 20 millimolar. The assay is initiated by placing the plate in a shaking water bath at 37° C. and is terminated after 10 min by rapid washing with multiple changes of 4° C. phosphate buffered saline (PBS). The radioactive Gly-Sar peptide that is transported by the HPEPT1 is extracted from the cell layer with 200 microliters of a one to one mixture of methanol and water and is counted in 4 ml of CytoScint ES™ scintillation cocktail (ICN). The data are plotted as % Gly-Sar uptake of control (no competitive substrate) versus the competitive substrate concentration. The $IC_{50}$, defined as that concentration which inhibits 50% of the uptake of the Gly-Sar uptake, indicates the degree of affinity that the test prodrug has for the HPEPT1. Typically, values that are below 10 mM indicate that the drug interacts with transporter.

Example 13

Determination of Prodrug Uptake Mediated by an Intestinal Transporter

Hela cells that overexpress HPEPT1 are incubated with a prodrug at a concentration of 50 micromolar in pH 6.0 uptake buffer for 45 minutes. The uptake reaction is stopped by washing of the cells with ice cold PBS three times. The cell layers are collected, the cells lysed, and the amounts of parent and prodrug in the cell lysate are determined by high performance liquid chromatography (HPLC). The uptake experiments are repeated in control cultures that do not overexpress the HPEPT1. The ratio of the test versus control values provides a measure of uptake efficiency for the prodrug by the HPEPT1 transporter.

Example 14

Testing for Activation of Prodrugs with Intestinal Cell Lysates and Plasma

Confluent Caco-2 cells are washed with phosphate buffer saline (PBS, pH 7.4) and are harvested with 0.05% Trypsin-EDTA at 37° C. for 5-10 min. Trypsin was neutralized by adding DMEM. The cells are washed off the plate and spun down by centrifugation. The pelleted cells are washed twice with pH 7.4 phosphate buffer (10 mM), and resuspended in pH 7.4 phosphate buffer (10 mM) to obtain a final concentration of approximately $4.70 \times 10^6$ cells/mL. The cells are lysed with one volume 0.5% Triton-X 100 solution. The cell lysate is homogenized by vigorous pipeting and total protein is quantified with the BioRad DC Protein Assay using bovine serum albumin as a standard. The hydrolysis reactions are carried out in 96-well plates (Corning, Corning, N.Y.). Caco-2 cell suspension (230 microliters) is placed in triplicate wells and the reactions are started with the addition of substrate and incubated at 37° C. At various time points, 40 microliter aliquots are removed and added to two volumes of 10% ice-cold TFA. The mixtures are centrifuged for 10 min at 1800 rcf and 4° C. and the supernatant filtered through a 0.45 micron pore size filter. The recovered filtrate is analyzed by HPLC.

To test stability in human plasma, 230 microliters of undiluted plasma is added to each well in triplicate and 40 microliters of substrate is added to start the reactions which are conducted at 37° C. for up to 4 hours. At various predetermined time points, 40 microliter aliquots are removed and added to two volumes of 10% ice-cold TFA. The mixtures are centrifuged for 10 min at 1800 rcf at 4° C. and the supernatant is filtered through a 0.45 micron pore size filter. The recovered filtrate is analyzed by HPLC.

The estimated half-lives ($t_{1/2}$) of the prodrugs are obtained from linear regression of pseudo-first-order plots of prodrug concentration vs time.

Example 15

Synthesis of GOC L Val Prodrug

The synthesis of GOC L Val prodrug is shown in Scheme 6.

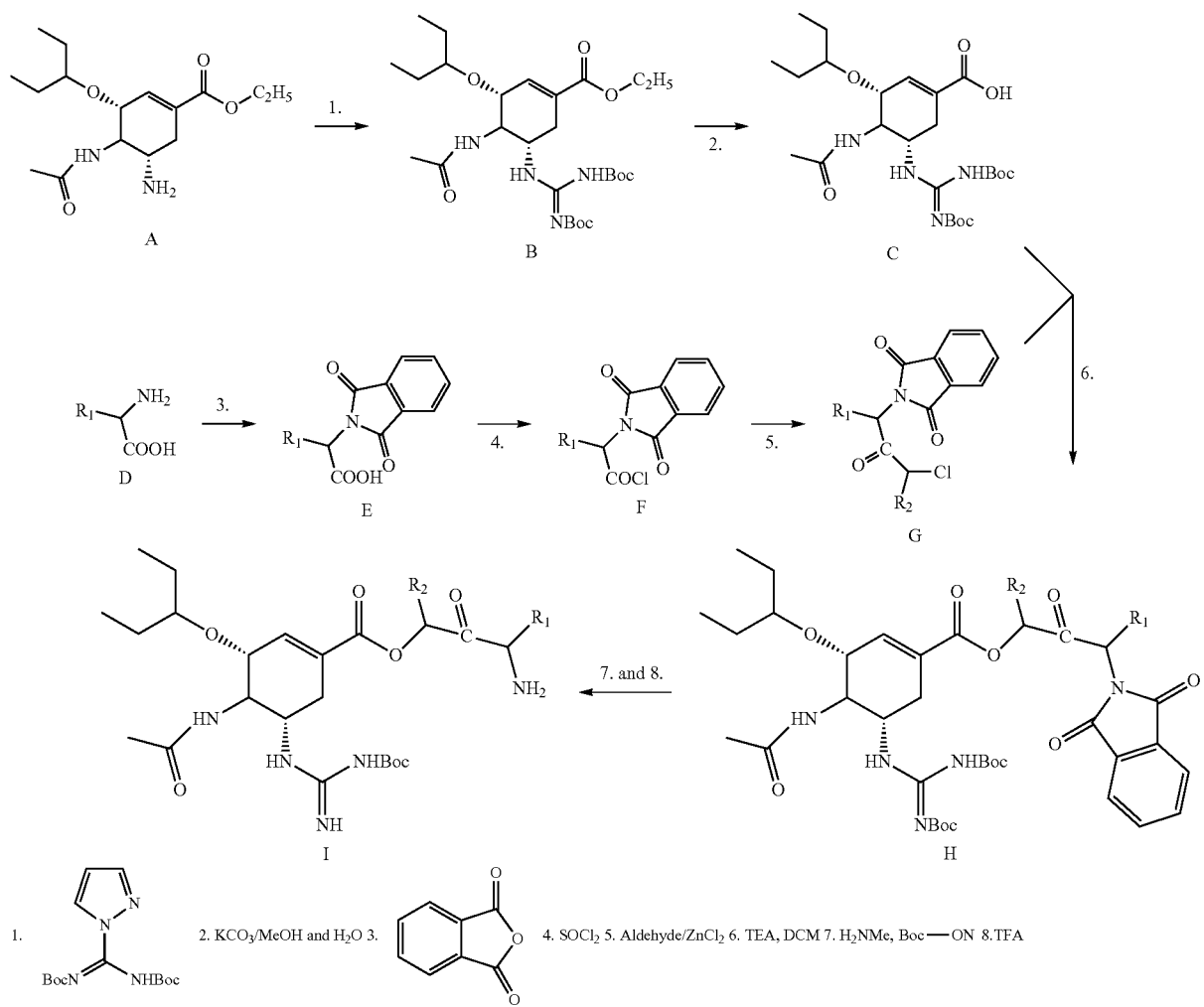

Scheme 6

1. 
   BocN—(pyrazole)—NHBoc
2. KCO₃/MeOH and H₂O
3. (phthalic anhydride)
4. SOCl₂
5. Aldehyde/ZnCl₂
6. TEA, DCM
7. H₂NMe, Boc—ON
8. TFA Synthesis of B:
N,N'-Di-Boc-1H-pyrazole-1-carboxamidine and proper amine are added to oseltamivir monophosphate (A) in THF. The reaction mixture is stirred until no more starting material is observed. The volatile components are removed by rotary evaporator. The residue is re-dissolved in EtOAc and subjected to flash chromatography for purification.

Synthesis of C:
Compound B is dissolved in mixture of 9:1 methanol and water. Potassium carbonate is added. The reaction mixture is stirred for one hour before several drops of acetic acid is added to neutralize the solution. After removal of the volatile components, the residue is re-dissolved in EtOAc and subject to flash chromatography for purification.

Synthesis of E:
Phthalic anhydride is added to L-valine (D) in toluene with presence of triethyl amine. After reflux for 24 hours, the solvent is removed by evaporation and the residue is purified by recrystallization from ethanol.

Synthesis of G:
Oxalyl chloride is added to solution of E in DCM. After refluxing for 30 minutes, the volatile components are evaporated and the residue is purified by recrystallization from DMC and hexane under argon environment. The product (F) is dried overnight under high vacuum before it can react with aldehyde by catalyzing with ZnCl₂ in DCM at 0 degree C. At the end of reaction, the reaction mixture is passed through a plug of Al₂O₃ to obtain product G with purity at 95%. No further purification is necessary.

Synthesis of H:
Compound G and C are dissolved in DCM. Triethyl amine is added with stirring. After 4 hours reaction, solid precipitate is removed by filtration. The filtrate is concentrated by rotary evaporator. The residue is re-dissolved in EtOAc and subjected to flash chromatography for purification.

Synthesis of I:
To the solution of Compound H in DCM, 2N methylamine in methanol is added. The reaction mixture is stirred for 5 minutes. Then all volatile components are removed by rotary evaporator. Dry-ice/acetone trapper is used to collect methylamine to prevent environmental hazard. The residue is re-dissolved in H₂O and dioxane. Boc-ON is added followed with triethylamine. The mixture is stirred overnight and extracted with EtOAc (2×100 mL). The organic phase is dried over anhydrous $Na_2SO_4$, filtered, and concentrated. After purification via column chromatography, the product is dissolved in TFA/DCM (1:4). The mixture is stirred for 4 hours. TFA and DCM are removed by rotary evaporator. Diethyl-ether is added to the residue to solidify the product that is further purified with preparative HPLC.

Example 16

Synthesis of GOC 1-Me PG L Val Prodrug

The synthesis of GOC 1-Me PG L Val is shown in Scheme 7.

stirred for one hour before several drops of acetic acid is added to neutralize the solution. After removal of the volatile components, the residue is re-dissolved in EtOAc and subject to flash chromatography for purification.
Synthesis of E:

To a solution of 1,2-propenyldiol in DMF is added TBDMSi and DMAP, followed with triethylamine. White precipitate is formed immediately. After stirring for 18 hours, N-Boc-L-valine and DCC are added. After another stirring of 12 hours, white precipitate is removed by filtration. The filtrate is concentrated by rotary evaporator. The residue is re-dissolved in EtOAc and purified via flash chromatography.
Synthesis of F To compound E is added 1M TBAF in THF and one mole equivalent AcOH. After stirring for 45 minutes, the mixture is

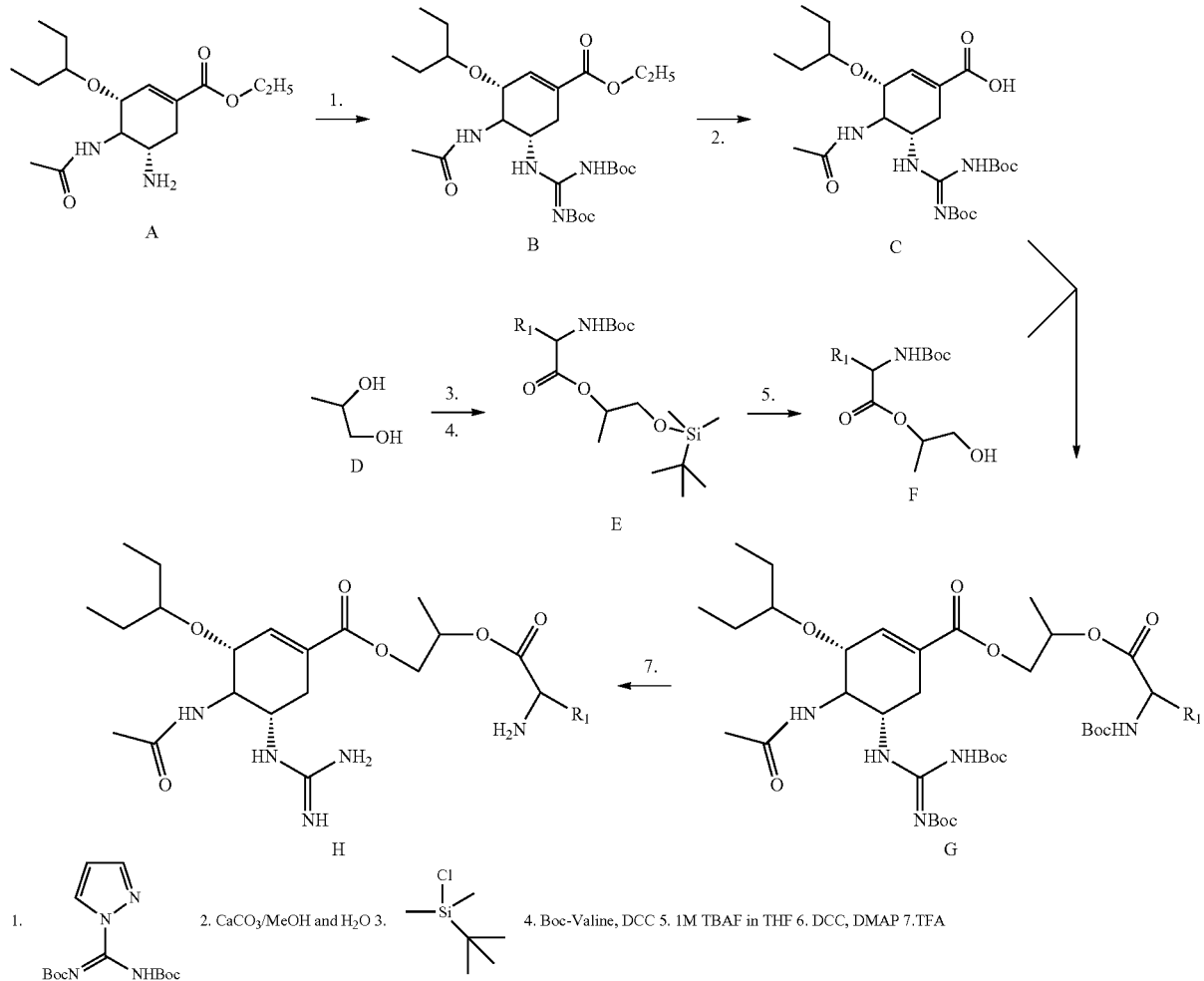

filtered through a silica gel plug. The filtrate is concentrated. The residue is re-dissolved in EtOAc and purified via flash chromatography.

Synthesis of G:

DCC and DMAP are added to solution of compound F and C in DMF. After stirring for 14 hours, the white precipitate is filtered off. The filtrate is concentrated by rotary evaporator. The residue is re-dissolved in EtOAc and subjected to flash chromatography for purification.

Synthesis of B:

N,N'-Di-Boc-1H-pyrazole-1-carboxamidine and proper amine are added to oseltamivir monophosphate (A) in THF. The reaction mixture is stirred until no more starting material is observed. The volatile components are removed by rotary evaporator. The residue is re-dissolved in EtOAc and subjected to flash chromatography for purification.
Synthesis of C:

Compound B is dissolved in mixture of 9:1 methanol and water. Potassium carbonate is added. The reaction mixture is Synthesis of H:

The compound G is dissolved in TFA/DCM (1:4). The mixture is stirred for 4 hours. TFA and DCM are removed by rotavapor. Diethylether is added to the residue to solidify the product that is further purified with preparative HPLC.

Example 17

Synthesis of GOC GlyOH L Val Prodrug

The synthesis of GOC GlyOH L Val prodrug is shown in Scheme 8.

components, the residue is re-dissolved in EtOAc and subject to flash chromatography for purification.

Synthesis of E:

To a solution of ethanolamine in DMF is added TBDMSi and DMAP, followed with triethylamine. White precipitate is formed immediately. After stirring for 18 hours, N-Boc-L-valine and DCC are added. After another stirring of 12 hours, white precipitate is removed by filtration. The filtrate is concentrated by rotary evaporator. The residue is re-dissolved in EtOAc and purified via flash chromatography.

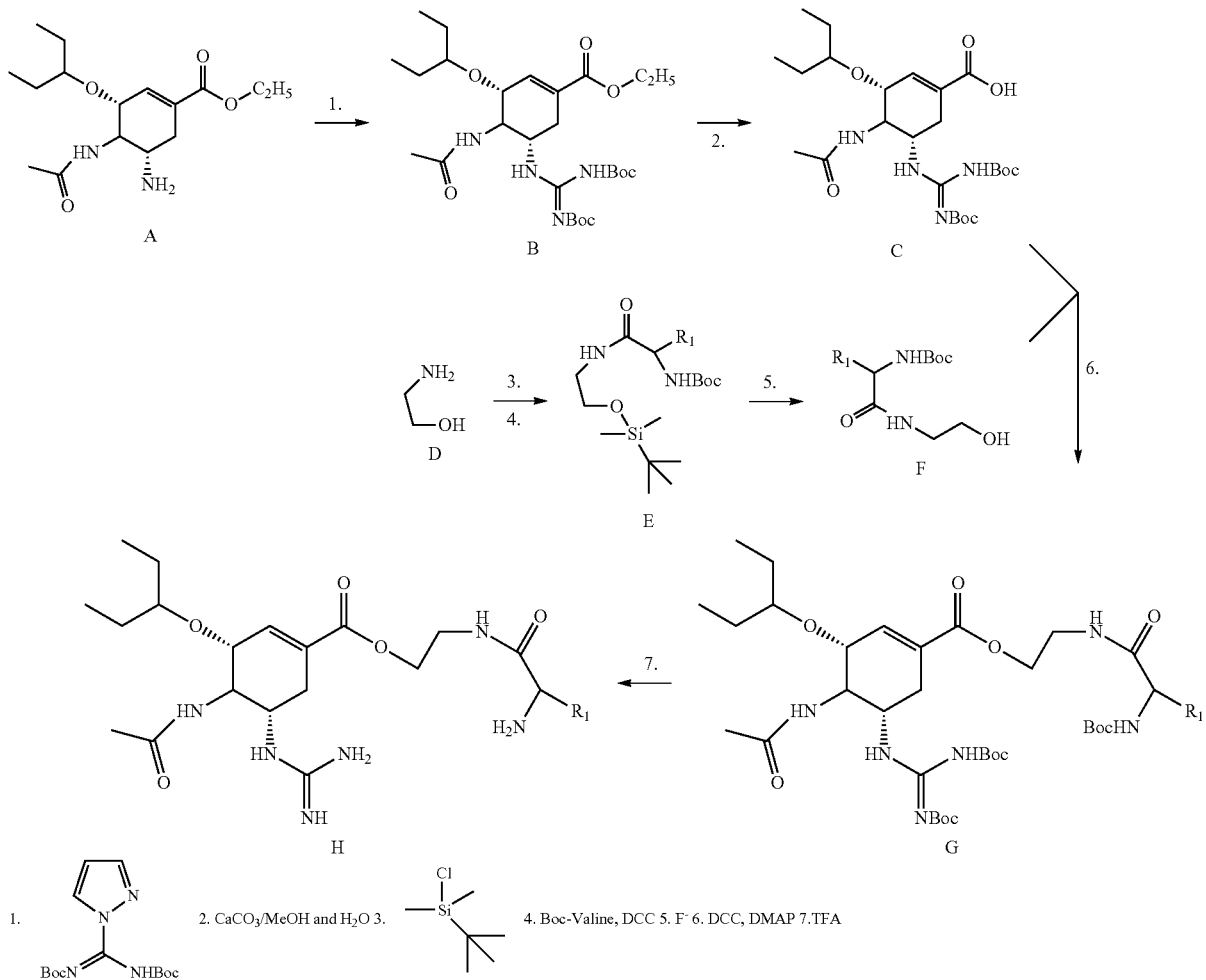

Synthesis of B:

N,N'-Di-Boc-1H-pyrazole-1-carboxamidine and proper amine are added to oseltamivir monophosphate (A) in THF. The reaction mixture is stirred until no more starting material be observed. The volatile components are removed by rotary evaporator. The residue is re-dissolved in EtOAc and subjected to flash chromatography for purification.

Synthesis of C:

Compound B is dissolved in mixture of 9:1 methanol and water. Potassium carbonate is added. The reaction mixture is stirred for one hour before several drops of acetic acid is added to neutralize the solution. After removal of the volatile Synthesis of F:

To compound E is added 1M TBAF in THF and one mole equivalent AcOH. After stirring for 45 minutes, the mixture is filtered through a silica gel plug. The filtrate is concentrated. The residue is re-dissolved in EtOAc and purified via flash chromatography.

Synthesis of G:

DCC and DMAP are added to solution of compound F and C in DMF. After stirring for 14 hours, the white precipitate is filtered off. The filtrate is concentrated by rotary evaporator. The residue is re-dissolved in EtOAc and subjected to flash chromatography for purification.

Synthesis of H:

The compound G is dissolved in TFA/DCM (1:4). The mixture is stirred for 4 hours. TFA and DCM are removed by rotary evaporator. Diethylether is added to the residue to solidify the product that is further purified with preparative HPLC.

Example 18

Bioavailability of GOC Prodrugs 10 mg-eq/kg of GOC or GOC prodrugs were directly injected to duodenum segment of fasted rats. 1 mg/kg of GOC was intravenously injected to calculate oral bioavailability of prodrugs. Appropriate volume of blood samples was taken from the jugular vein at the predetermined time points.

Rat plasma samples were analyzed for GOC prodrug and GOC using LCMSMS following solid phase extraction sampling preparation. A reverse phase solid-phase cartridge (HLB, 30 mg/1 cc, Waters) was activated with 1.0 mL of methanol and equilibrated with 1.0 mL of water. A 250 ul aliquot of rat plasma was acidified with 250 uL of 1% TFA solution and loaded on to the cartridges. After washing with 1.0 ml water, the compounds are eluted with 1 ml of 2% acetic acid solution. The eluted solvent was evaporated under nitrogen stream in TurboVap and the residue was reconstituted in 250 ul of mobile phase.

Samples were analyzed using a LC/MS/MS system (Micromass Quattro II, HP 1100). The HPLC system consisted of a HP1100 system (Hewlett Packard, CA). 10 ul of sample was separated with a C18 column (2.1×150 mm) using a mobile phase of 10-30% acetonitrile:water containing 0.1% formic acid. Quattro II triple quadrupole mass spectrometer (Micromass, Beverly, Mass.) interfaced with the HPLC via electropray source was used for the mass analysis and detection. The data acquisition software was MassLynx (version 4.0). Calibration curves were constructed by weighted (1/x) least square regression of peak area versus concentrations of the calibration standards.

Bioavailability of prodrugs following open gut direct injection are summarized in Table 3. GOC L-Val showed 16.2% of bioavailability among the prodrugs tested, at least 4 fold increase compared to GOC. Bioavailability of Gilead GOC neuraminidase prodrugs are summarized for reference in Table 4. Bioavailability calculation is based on the AUC0-4 hrs. GOC L-Val is breaking down completely to GOC and GOC is the major metabolite in the plasma. Only a trace amount of GOC is detected in the plasma following GOC GlyOH L-Val dose. The majority of the dose is detected as prodrug.

TABLE 3

AUC and bioavailability following IV injection (1 mg/kg) of GOC or duodenal administration (OGI) of 10 mg-eq/kg of GOC or GOC prodrugs to rat duodenum.

| Compound | Route | $AUC_{0-4\,hr}$ (ng/mL) · hrs | | | % F |
|---|---|---|---|---|---|
| | | GOC | Prodrug | Total AUC | |
| GOC | IV | 385 ± 167 | N/A | 385 ± 167 | 100.0 |
| GOC | OGI | 265 ± 91 | N/A | 265 ± 91 | 4.6 |
| GOC PG L-Val | OGI | 98 ± 49 | 17 ± 12 | 116 ± 61 | 2.0 |
| GOC L-Val | OGI | 935 ± 324 | 0 | 935 ± 324 | 16.2 |
| GOC GlyOH L-Val | OGI | 15 ± 13 | 386 ± 406 | 401 ± 419 | 6.9 |

TABLE 4

Bioavailability of Gilead neuraminidase inhibitors (prodrugs of oseltamivir carboxylate or guanidino oseltamivir carboxylate) administered as 10 mg-eq/kg oral gavage to rats (see [21])

| Compound | Cmax (ng/mL) | % F |
|---|---|---|
| GS4071 (OC) | 30 | 4.3 |
| GS4104 (Ethyl ester of GS4071) | 47 | 35 |
| GS4116 (GOC) | 60 | 4.0 |
| GS4109 (Ethyl ester of GS4116) | 30 | 2.1 |
| Zanamivir (GG167) | 60 | 3.7 |

REFERENCES

1. Albert, A., Chemical aspects of selective toxicity. Nature 1958. 182(4633): p. 421-2.
2. Amsberry, K. L., A. E. Gerstenberger, and R. T. Borchardt, Amine prodrugs which utilize hydroxy amide lactonization. II. A potential esterase-sensitive amide prodrug. Pharm Res, 1991. 8(4): p. 455-61.
3. Ettmayer, P., et al., Lessons learned from marketed and investigational prodrugs. J Med Chem, 2004. 47(10): p. 2393-404.
4. Fleisher, D., R. Bong, and B. H. Stewart, Improved oral drug delivery: solubility limitations overcome by the use of prodrugs. Advanced Drug Delivery Reviews, 1996. 19(2): p. 115-130.
5. Kearney, A. S., Prodrugs and targeted drug delivery. Advanced Drug Delivery Reviews, 1996. 19(2): p. 225-239.
6. Sinhababu, A. K. and D. R. Thakker, Prodrugs of anticancer agents. Advanced Drug Delivery Reviews, 1996. 19(2): p. 241-273.
7. Stella, V. J., et al., eds. Prodrugs: Challenges and Rewards, Parts 1 and 2 1 ed. Biotechnology: Pharmaceutical Aspects, ed. R. T. Borchardt and C. R. Middaugh. 2007, Springer-Verlag New York, LLC. 1470
8. Testa, B. and J. M. Mayer, Hydrolysis in Drug and Prodrug Metabolism: Chemistry, Biochemistry, and Enzymology. 1 ed. 2003: John Wiley & Sons Canada Ltd. 800.
9. Landowski, C. P., et al., Nucleoside ester prodrug substrate specificity of liver carboxylesterase. J Pharmacol Exp Ther, 2006. 316(2): p. 572-80.
10. Liederer, B. M. and R. T. Borchardt, Enzymes involved in the bioconversion of ester-based prodrugs. J Pharm Sci, 2006. 95(6): p. 1177-95.
11. Kim, I., et al., Identification of a Human Valacyclovirase. Biphenyl Hydrolase-like Protein as Valacyclovir Hydrolase. Journal of Biological Chemistry, 2003. 278(28): p. 25348-25356.
12. Kim, I., G. M. Crippen, and G. L. Amidon, Structure and specificity of a human valacyclovir activating enzyme: a homology model of BPHL. Mol Pharm, 2004. 1(6): p. 434-46.
13. Weller, S., et al., Pharmacokinetics of the acyclovir prodrug valaciclovir after escalating single- and multiple-dose administration to normal volunteers. Clinical pharmacology and therapeutics 1993. 54(6): p. 595-605.
14. Soul-Lawton, J., et al., Absolute bioavailability and metabolic disposition of valaciclovir, the L-valyl ester of acyclovir, following oral administration to humans. Antimicrobial Agents and Chemotherapy, 1995. 39(12): p. 2759-64.
15. Landowski, C. P., et al., Gene expression in the human intestine and correlation with oral valacyclovir pharmacokinetic parameters. Journal of Pharmacology and Experimental Therapeutics, 2003. 306(2): p. 778-786.
16. Ganaphthy, M. E., et al., Valacyclovir: a substrate for the intestinal and renal peptide transporters PEPT1 and PEPT2. Biochemical and Biophysical Research Communications, 1998. 246(2): p. 470-475.
17. Balimane, P. V., et al., Direct evidence for peptide transporter (PepT1)-mediated uptake of a nonpeptide prodrug, valacyclovir. Biochemical and Biophysical Research Communications, 1998. 250(2): p. 246-251.
18. Sugawara, M., et al., Transport of valganciclovir, a ganciclovir prodrug, via peptide transporters PEPT1 and PEPT2. Journal of Pharmaceutical Sciences, 2000. 89(6): p. 781-789.
19. Kim, C. U., et al., Influenza Neuraminidase Inhibitors Possessing a Novel Hydrophobic Interaction in the Enzyme Active Site: Design, Synthesis, and Structural Analysis of Carbocyclic Sialic Acid Analogs with Potent Anti-Influenza Activity. Journal of the American Chemical Society, 1997. 119(4): p. 681-690.
20. He, G., J. Massarella, and P. Ward, Clinical pharmacokinetics of the prodrug oseltamivir and its active metabolite Ro 64-0802. Clinical Pharmacokinetics, 1999. 37(6): p. 471-484.
21. Li, W., et al., Identification of GS 4104 as an orally bioavailable prodrug of the influenza virus neuraminidase inhibitor GS 4071. Antimicrob Agents Chemother, 1998. 42(3): p. 647-53.
22. Liu, Y., M. P. Patricelli, and B. F. Cravatt, Activity-based protein profiling: the serine hydrolases. Proc Natl Acad Sci USA, 1999. 96(26): p. 14694-9.
23. Bromme, D., et al., Potent and selective inactivation of cysteine proteinases with N-peptidyl-O-acyl hydroxylamines. Biochem J, 1989. 263(3): p. 861-6.
24. Kumar, S., et al., Activity-based probes for protein tyrosine phosphatases. Proc Natl Acad Sci USA, 2004. 101(21): p. 7943-8.
25. Kidd, D., Y. Liu, and B. F. Cravatt, Profiling serine hydrolase activities in complex proteomes. Biochemistry, 2001. 40(13): p. 4005-15.
26. Barglow, K. T. and B. F. Cravatt, Discovering disease-associated enzymes by proteome reactivity profiling. Chem Biol, 2004. 11(11): p. 1523-31.
27. Sieber, S. A., et al., Proteomic profiling of metalloprotease activities with cocktails of active-site probes. Nat Chem Biol, 2006. 2(5): p. 274-81.
28. Closs, E. I., et al., Plasma membrane transporters for arginine. J Nutr, 2004. 134(10 Suppl): p. 2752S-2759S; discussion 2765S-2767S.
29. Vig, B. S., et al., Human PEPT1 pharmacophore distinguishes between dipeptide transport and binding. J Med Chem, 2006. 49(12): p. 3636-44.
30. Biegel, A., et al., The renal type H(+)/peptide symporter PEPT2: structure-affinity relationships. Amino Acids, 2006. 31(2): p. 137-56.
31. Brandsch, M., I. Knutter, and F. H. Leibach, The intestinal H+/peptide symporter PEPT1: structure-affinity relationships. Eur J Pharm Sci, 2004. 21(1): p. 53-60.
32. Daniel, H., E. L. Morse, and S. A. Adibi, Determinants of substrate affinity for the oligopeptide/H+ symporter in the renal brush border membrane. J Biol Chem, 1992. 267(14): p. 9565-73.
33. Biegel, A., et al., Three-dimensional quantitative structure-activity relationship analyses of beta-lactam antibiotics and tripeptides as substrates of the mammalian H+/peptide cotransporter PEPT1. J Med Chem, 2005. 48(13): p. 4410-9.
34. Andersen, R., et al., Development of a QSAR model for binding of tripeptides and tripeptidomimetics to the human intestinal di-/tripeptide transporter hPEPT1. Pharm Res, 2006. 23(3): p. 483-92.
35. Brandsch, M., et al., Decisive structural determinants for the interaction of proline derivatives with the intestinal H+/peptide symporter. Eur J Biochem, 1999. 266(2): p. 502-8.
36. Biegel, A., et al., Structural requirements for the substrates of the H+/peptide cotransporter PEPT2 determined by three-dimensional quantitative structure-activity relationship analysis. J Med Chem, 2006. 49(14): p. 4286-96.
37. Shin, H. C., et al., Interaction of intestinal nucleoside transporter hCNT2 with amino acid ester prodrugs of floxuridine and 2-bromo-5,6-dichloro-1-beta-D-ribofuranosylbenzimidazole. Biol Pharm Bull, 2006. 29(2): p. 247-52.
38. Han, H., et al., 5'-Amino acid esters of antiviral nucleosides, acyclovir, and AZT are absorbed by the intestinal PEPT1 peptide transporter. Pharm Res, 1998. 15(8): p. 1154-9.
39. Landowski, C. P., et al., Floxuridine amino acid ester prodrugs: enhancing Caco-2 permeability and resistance to glycosidic bond metabolism. Pharm Res, 2005. 22(9): p. 1510-8.
40. Stewart, B. H., G. L. Amidon, and R. K. Brabec, Uptake of prodrugs by rat intestinal mucosal cells: mechanism and pharmaceutical implications. J Pharm Sci, 1986. 75(10): p. 940-5.
41. Buggs, C. W., et al., The Absorption, Distribution, And Excretion Of Streptomycin In Man. J Clin Invest, 1946. 25(1): p. 94-102.
42. Linkins, L. A. and J. I. Weitz, Pharmacology and clinical potential of direct thrombin inhibitors. Curr Pharm Des, 2005. 11(30): p. 3877-84.
43. Cass, L. M., C. Efthymiopoulos, and A. Bye, Pharmacokinetics of zanamivir after intravenous, oral, inhaled or intranasal administration to healthy volunteers. Clin Pharmacokinet, 1999. 36 Suppl 1: p. 1-11.
44. Pentikainen, P. J., P. J. Neuvonen, and A. Penttila, Pharmacokinetics of metformin after intravenous and oral administration to man. Eur J Clin Pharmacol, 1979. 16(3): p. 195-202.
45. Nicklin, P., et al., Transfer of metformin across monolayers of human intestinal Caco-2 cells and across rat intestine. International Journal of Pharmaceutics, 1996. 128(1-2): p. 155.
46. Dresser, M. J., et al., Interactions of n-tetraalkylammonium compounds and biguanides with a human renal organic cation transporter (hOCT2). Pharm Res, 2002. 19(8): p. 1244-7.
47. Shikata, E., et al., Human organic cation transporter (OCT1 and OCT2) gene polymorphisms and therapeutic effects of metformin. J Hum Genet, 2007. 52(2): p. 117-22.
48. Masuda, S., et al., Identification and functional characterization of a new human kidney-specific H+/organic cation antiporter, kidney-specific multidrug and toxin extrusion 2. J Am Soc Nephrol, 2006. 17(8): p. 2127-35.
49. Koepsell, H., Polyspecific organic cation transporters: their functions and interactions with drugs. Trends Pharmacol Sci, 2004. 25(7): p. 375-81.
50. Closs, E. I., et al., Interference of L-arginine analogs with L-arginine transport mediated by the y+ carrier hCAT-2B. Nitric Oxide, 1997. 1(1): p. 65-73.
51. Closs, E. I., et al., Structure and Function of Cationic Amino Acid Transporters (CATs). J Membr Biol, 2006. 213(2): p. 67-77.

52. Closs, E. I., et al., Human cationic amino acid transporters hCAT-1, hCAT-2A, and hCAT-2B: three related carriers with distinct transport properties. Biochemistry, 1997. 36(21): p. 6462-8.
53. Verrey, F., et al., CATs and HATs: the SLC7 family of amino acid transporters. Pflugers Arch, 2004. 447(5): p. 532-42.
54. Busch, A. E., et al., Human neurons express the polyspecific cation transporter hOCT2, which translocates monoamine neurotransmitters, amantadine, and memantine. Mol Pharmacol, 1998. 54(2): p. 342-52.
55. Ohashi, R., et al., Studies on functional sites of organic cation/carnitine transporter OCTN2 (SLC22A5) using a Ser467Cys mutant protein. J Pharmacol Exp Ther, 2002. 302(3): p. 1286-94.
56. White, D. L., et al., OCT-1-mediated influx is a key determinant of the intracellular uptake of imatinib but not nilotinib (AMN107): reduced OCT-1 activity is the cause of low in vitro sensitivity to imatinib. Blood, 2006. 108(2): p. 697-704.
57. Wu, X., et al., Structure, function, and regional distribution of the organic cation transporter OCT3 in the kidney. Am J Physiol Renal Physiol, 2000. 279(3): p. F449-58.
58. Yabuuchi, H., et al., Novel membrane transporter OCTN1 mediates multispecific, bidirectional, and pH-dependent transport of organic cations. J Pharmacol Exp Ther, 1999. 289(2): p. 768-73.
59. Zhang, L., M. E. Schaner, and K. M. Giacomini, Functional characterization of an organic cation transporter (hOCT1) in a transiently transfected human cell line (HeLa). J Pharmacol Exp Ther, 1998. 286(1): p. 354-61.
60. Moscona, A., Neuraminidase inhibitors for influenza. N Engl J Med, 2005. 353(13): p. 1363-73.
61. Masuda, H., et al., Incidence of amantadine-resistant influenza A viruses in sentinel surveillance sites and nursing homes in Niigata, Japan. Microbiol. Immunol, 2000. 44(10): p. 833-9.
62. Monto, A. S., Vaccines and antiviral drugs in pandemic preparedness. Emerg Infect Dis, 2006. 12(1): p. 55-60.
63. Wetherall, N. T., et al., Evaluation of neuraminidase enzyme assays using different substrates to measure susceptibility of influenza virus clinical isolates to neuraminidase inhibitors: report of the neuraminidase inhibitor susceptibility network. J Clin Microbiol, 2003. 41(2): p. 742-50.
64. Le, Q. M., et al., Avian flu: isolation of drug-resistant H5N1 virus. Nature, 2005. 437(7062): p. 1108.
65. Zurcher, T., et al., Mutations conferring zanamivir resistance in human influenza virus N2 neuraminidases compromise virus fitness and are not stably maintained in vitro. J Antimicrob Chemother, 2006. 58(4): p. 723-32.
66. Eid, A. J., et al., Clinical features and outcomes of cytomegalovirus retinitis after transplantation. Transpl Infect Dis, 2008. 10(1): p. 13-8.
67. Peters, B. S., et al., Cytomegalovirus infection in AIDS. Patterns of disease, response to therapy and trends in survival. J Infect, 1991. 23(2): p. 129-37.
68. Sakr, M., et al., Cytomegalovirus infection of the upper gastrointestinal tract following liver transplantation—incidence, location, and severity in cyclosporine- and FK506-treated patients. Transplantation, 1992. 53(4): p. 786-91.
69. Doniger, J., S. Muralidhar, and L. J. Rosenthal, Human cytomegalovirus and human herpesvirus 6 genes that transform and transactivate. Clin Microbiol Rev, 1999. 12(3): p. 367-82.
70. Sinzger, C., et al., Fibroblasts, epithelial cells, endothelial cells and smooth muscle cells are major targets of human cytomegalovirus infection in lung and gastrointestinal tissues. J Gen Virol, 1995. 76 (Pt 4): p. 741-50.
71. Qiu, X., et al., Unique fold and active site in cytomegalovirus protease. Nature, 1996. 383(6597): p. 275-9.
72. Gilbert, C. and G. Boivin, Human cytomegalovirus resistance to antiviral drugs. Antimicrob Agents Chemother, 2005. 49(3): p. 873-83.
73. Matusick-Kumar, L., et al., The C-terminal 25 amino acids of the protease and its substrate ICP35 of herpes simplex virus type 1 are involved in the formation of sealed capsids. J Virol, 1995. 69(7): p. 4347-56.
74. Tong, L., et al., A new serine-protease fold revealed by the crystal structure of human cytomegalovirus protease. Nature, 1996. 383(6597): p. 272-5.
75. Shieh, H. S., et al., Three-dimensional structure of human cytomegalovirus protease. Nature, 1996. 383(6597): p. 279-82.
76. Hara, K., et al., Inhibition of the protease activity of influenza virus RNA polymerase PA subunit by viral matrix protein. Microbiol. Immunol, 2003. 47(7): p. 521-6.
77. Engelhardt, O. G. and E. Fodor, Functional association between viral and cellular transcription during influenza virus infection. Rev Med Virol, 2006. 16(5): p. 329-45.
78. Hara, K., et al., Influenza virus RNA polymerase PA subunit is a novel serine protease with Ser624 at the active site. Genes Cells, 2001. 6(2): p. 87-97.
79. Song, X., et al., Amino acid ester prodrugs of the antiviral agent 2-bromo-5,6-dichloro-1-(beta-D-ribofuranosyl) benzimidazole as potential substrates of hPEPT1 transporter. J Med Chem, 2005. 48(4): p. 1274-7.
80. Mittal, S., et al., Prolidase, a potential enzyme target for melanoma: design of proline-containing dipeptide-like prodrugs. Mol Pharm, 2005. 2(1): p. 37-46.
81. Connors, K. A., Amidon, G. L., Stella, V. J., Chemical Stability of Pharmaceuticals: A Handbook for Pharmacists Second ed. 1986: Wiley-Interscience
82. Rautio, J., et al., Synthesis and in vitro evaluation of aminoethoxyalkyl esters of 2-(6-methoxy-2-naphthyl)propionic acid as novel naproxen prodrugs for dermal drug delivery. Pharm Res, 1999. 16(8): p. 1172-8.
83. Kim, I., et al., A novel nucleoside prodrug-activating enzyme: substrate specificity of biphenyl hydrolase-like protein. Mol Pharm, 2004. 1(2): p. 117-27.
84. Vig, B. S., et al., Amino acid ester prodrugs of floxuridine: synthesis and effects of structure, stereochemistry, and site of esterification on the rate of hydrolysis. Pharm Res, 2003. 20(9): p. 1381-8.
85. Landowski, C. P., et al., Targeted delivery to PEPT1-overexpressing cells: acidic, basic, and secondary floxuridine amino acid ester prodrugs. Mol Cancer Ther, 2005. 4(4): p. 659-67.
86. Song, X., et al., Amino acid ester prodrugs of the anticancer agent gemcitabine: synthesis, bioconversion, metabolic bioevasion, and hPEPT1-mediated transport. Mol Pharm, 2005. 2(2): p. 157-67.
87. Bergman, A. M., H. M. Pinedo, and G. J. Peters, Determinants of resistance to 2',2'-difluorodeoxycytidine (gemcitabine). Drug Resist Updat, 2002. 5(1): p. 19-33.
88. Bouffard, D. Y., J. Laliberte, and R. L. Momparler, Kinetic studies on 2',2'-difluorodeoxycytidine (Gemcitabine) with purified human deoxycytidine kinase and cytidine deaminase Biochem Pharmacol, 1993. 45(9): p. 1857-61.
89. Chabner, B. A., et al., Purification and properties of cytidine deaminase from normal and leukemic granulocytes. J Clin Invest, 1974. 53(3): p. 922-31.

90. Heinemann, V., et al., Comparison of the cellular pharmacokinetics and toxicity of 2',2'-difluorodeoxycytidine and 1-beta-D-arabinofuranosylcytosine. Cancer Res, 1988. 48(14): p. 4024-31.
91. Plunkett, W., et al., Gemcitabine: metabolism, mechanisms of action, and self-potentiation. Semin Oncol, 1995. 22(4 Suppl 11): p. 3-10.
92. Lorenzi, P. L., et al., N-methylpurine DNA glycosylase and 8-oxoguanine dna glycosylase metabolize the antiviral nucleoside 2-bromo-5,6-dichloro-1-(beta-D-ribofuranosyl)benzimidazole. Drug Metab Dispos, 2006. 34(6): p. 1070-7.
93. Lorenzi, P. L., et al., Amino acid ester prodrugs of 2-bromo-5,6-dichloro-1-(beta-D-ribofuranosyl)benzimidazole enhance metabolic stability in vitro and in vivo. J Pharmacol Exp Ther, 2005. 314(2): p. 883-90.
94. Mittal, S., et al., Proline prodrug of melphalan targeted to prolidase, a prodrug activating enzyme overexpressed in melanoma. Pharm Res, 2007. 24(7): p. 1290-8.
95. Mittal, S., et al., Proline prodrug of melphalan, prophalan-L, demonstrates high therapeutic index in a murine melanoma model, Eur J Pharm Biopharm, 2007. In Press, Corrected Proof, Available online 4 Apr. 2007.
96. Shi, D., et al., Anti-influenza prodrug oseltamivir is activated by carboxylesterase human carboxylesterase 1, and the activation is inhibited by antiplatelet agent clopidogrel. J Pharmacol Exp Ther, 2006. 319(3): p. 1477-84.
97. Guzzo, P. R., et al., Preparation of optically active (ethoxy)alkyl esters from optically active O-acyl-[alpha]-hydroxy acids. Tetrahedron Letters, 2002. 43(32): p. 5685-5689.
98. Stella, V. J., W. N. Charman, and V. H. Naringrekar, Prodrugs. Do they have advantages in clinical practice? Drugs, 1985. 29(5): p. 455-73.
99. Babu, Y. S., et al., BCX-1812 (RWJ-270201): discovery of a novel, highly potent, orally active, and selective influenza neuraminidase inhibitor through structure-based drug design. J Med Chem, 2000. 43(19): p. 3482-6.
100. Bantia, S., et al., Comparison of the anti-influenza virus activity of RWJ-270201 with those of oseltamivir and zanamivir. Antimicrob Agents Chemother, 2001. 45(4): p. 1162-7.
101. Smee, D. F., et al., Cyclopentane neuraminidase inhibitors with potent in vitro anti-influenza virus activities. Antimicrob Agents Chemother, 2001. 45(3): p. 743-8.
102. Sidwell, R. W., et al., In vivo influenza virus-inhibitory effects of the cyclopentane neuraminidase inhibitor RJW-270201. Antimicrob Agents Chemother, 2001. 45(3): p. 749-57.
103. Bantia, S., et al., Anti-influenza virus activity of peramivir in mice with single intramuscular injection. Antiviral Res, 2006. 69(1): p. 39-45.
104. Martin, R., K. L. Witte, and C.-H. Wong, The synthesis and enzymatic incorporation of sialic acid derivatives for use as tools to study the structure, activity, and inhibition of glycoproteins and other glycoconjugates. Bioorganic & Medicinal Chemistry, 1998. 6(8): p. 1283-1292.
105. Malcolm Chandler, M. J. B., Richard Conroy, Brian Lamount, Bina Patel, Vipulkumar K. Patel, Ian P. Steeples, Richard Storer, Naill G. Weir, Michael Wrightm Christopher Williamson, Synthesis of the potent influenza neuraminidase inhibitor 4-guanidino Neu5Ac2en. X-Ray molecular structure of 5-acetamido-4-amino-2,6-anhydro-3,4,5-trideoxy-D-erythro-L-gluco-nononic acid. J. Chem. Soc., Perkin Trans. 1, 1995: p. 1173-1180.
106. Masuda, T., et al., Synthesis and anti-influenza evaluation of polyvalent sialidase inhibitors bearing 4-guanidino-Neu5Ac2en derivatives. Chem Pharm Bull (Tokyo), 2003. 51(12): p. 1386-98.
107. Nudelman, A., et al., Prodrugs of butyric acid. Novel derivatives possessing increased aqueous solubility and potential for treating cancer and blood diseases. Eur J Med Chem, 2001. 36(1): p. 63-74.
108. Gomes, P., et al., Improved Synthesis of Amino Acid and Dipeptide Chloromethyl Esters Using Bromochloromethane. Synthetic Communications, 2003. 33(10): p. 1683-1693.
109. Shitara, E., et al., Synthesis of 6-acetamido-5-amino- and -5-guanidino-3,4-dehydro-N-(2-ethylbutyryl)-3-piperidinecarboxylic acids related to zanamivir and oseltamivir, inhibitors of influenza virus neuraminidases. Org Lett, 2000. 2(24): p. 3837-40.
110. Saulnier, M. G., et al., An efficient method for the synthesis of guanidino prodrugs. Bioorganic & Medicinal Chemistry Letters, 1994. 4(16): p. 1985.
111. Han, H. K., D. M. Oh, and G. L. Amidon, Cellular uptake mechanism of amino acid ester prodrugs in Caco-2/hPEPT1 cells overexpressing a human peptide transporter. Pharm Res, 1998. 15(9): p. 1382-6.
112. Hermann, J. C., et al., Predicting substrates by docking high-energy intermediates to enzyme structures. J Am Chem Soc, 2006. 128(49): p. 15882-91.
113. Hermann, J. C., et al., Structure-based activity prediction for an enzyme of unknown function. Nature, 2007. 448 (7155): p. 775-9.
114. Tantillo, D. J. and K. N. Houk, Transition state docking: a probe for noncovalent catalysis in biological systems. Application to antibody-catalyzed ester hydrolysis. J Comput Chem, 2002. 23(1): p. 84-95.
115. Stevens, J. T., et al., In vitro proteolytic activity and active-site identification of the human cytomegalovirus protease. Eur J Biochem, 1994. 226(2): p. 361-7.
116. Bonneau, P. R., et al., Design of fluorogenic peptide substrates for human cytomegalovirus protease based on structure-activity relationship studies. Anal Biochem, 1998. 255(1): p. 59-65.
117. Khayat, R., et al., Structural and biochemical studies of inhibitor binding to human cytomegalovirus protease. Biochemistry, 2003. 42(4): p. 885-91.
118. Ogilvie, W., et al., Peptidomimetic inhibitors of the human cytomegalovirus protease. J Med Chem, 1997. 40(25): p. 4113-35.
119. Kim, J. S., et al., The suitability of an in situ perfusion model for permeability determinations: utility for BCS class I biowaiver requests. Mol Pharm, 2006. 3(6): p. 686-94.
120. Amidon, G. L., P. J. Sinko, and D. Fleisher, Estimating human oral fraction dose absorbed: a correlation using rat intestinal membrane permeability for passive and carrier-mediated compounds. Pharm Res, 1988. 5(10): p. 651-4.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A prodrug of a neuraminidase inhibitor, the prodrug having the formula (III):

(III)

[Chemical structure showing compound with $R_{16}O$, $R_{17}O$, $OR_{16}$, HN, acetyl, $OR_{14}$, and guanidine group with $NR_{15}$, $R_{15}$—NH substituents]

where $R_{14}$ is —CH(CH$_3$)OC(O)(CH$_2$)$_n$CH(R')NH$_2$, —CH(CH$_3$)OC(O)(CH$_2$)$_n$CH(R')N(H)C(O)(CH$_2$)$_n$CH(R'')NH$_2$, or —CH(CH$_3$)OC(O)(CH$_2$)$_n$CH(R')N(H)C(O)(CH$_2$)$_n$CH(R'')N(H)C(O)(CH$_2$)$_n$CH(R''')NH$_2$;

n is zero or one;

$R_{15}$ is in each occurrence independently —C(O)OCH(CH$_3$)OC(O)(CH$_2$)$_n$CH(R')NH$_2$, —C(O)OCH(CH$_3$)OC(O)(CH$_2$)$_n$CH(R')N(H)C(O)(CH$_2$)$_n$CH(R''')NH$_2$, —CH(CH$_3$)O—C(O)(CH$_2$)$_n$CH(R')N(H)C(O)(CH$_2$)$_n$CH(R'')N(H)C(O)(CH$_2$)$_n$CH(R''')NH$_2$, or —H; each $R_{16}$ is independently —H, an amino acid residue having the formula —C(O)(CH$_2$)$_n$CH(R')NH$_2$, a dipeptide residue having the formula —C(O)(CH$_2$)$_n$CH(R')N(H)C(O)(CH$_2$)$_n$CH(R'')NH$_2$, or a tripeptide residue having the formula —CH(CH$_3$)O—C(O)(CH$_2$)$_n$CH(R')N(H)C(O)(CH$_2$)$_n$CH(R'')N(H)C(O)(CH$_2$)$_n$CH(R''')NH$_2$, where R', R'' and R''' are each an independently selected amino acid side chain; $R_{17}$ is H.

2. The prodrug of claim 1, wherein both occurrences of $R_{15}$ are H.

3. The prodrug of claim 2, wherein both occurrences of $R_{16}$ are H.

4. The prodrug of claim 1, wherein $R_{14}$ is CH(CH$_3$)OC(O)(CH$_2$)$_n$CH(R')NH$_2$, wherein n is zero.

5. The prodrug of claim 4, wherein R' is —CH(CH$_3$)$_2$, —CH(CH$_2$CH$_3$)(CH$_3$), —CH$_2$—CH(CH$_3$)$_2$, or —CH$_2$—[phenyl].

6. The prodrug of claim 5, wherein R' is —CH(CH$_3$)$_2$ or —CH(CH$_2$CH$_3$)(CH$_3$).

7. The prodrug of claim 1, having the structure:

[Chemical structure of prodrug with valine ester]

8. The prodrug of claim 1, having the structure:

[Chemical structure of prodrug with isoleucine ester]

9. A method of inhibiting an influenza virus infection in a subject comprising: administering a neuraminidase inhibitor prodrug of claim 1, to the subject.

10. The method of claim 9, wherein the subject is human.

* * * * *